(12) United States Patent
Goletti et al.

(10) Patent No.: US 7,785,607 B2
(45) Date of Patent: Aug. 31, 2010

(54) IMMUNE DIAGNOSTIC ASSAY TO DIAGNOSE AND MONITOR TUBERCULOSIS INFECTION

(75) Inventors: Delia Goletti, Rome (IT); Donatella Vincenti, Rome (IT); Stefania Carrara, Rome (IT); Enrico Girardi, Rome (IT); Fabrizio Poccia, Rome (IT); Rita Casetti, Cave (IT); Massimo Amicosante, Rome (IT)

(73) Assignee: Istituto Nazionale Delle Malattie Infettive "Lazzaro Spallanzani" IRCCS, Rome (IT)

( * ) Notice: Subject to any disclaimer, the term of this patent is extended or adjusted under 35 U.S.C. 154(b) by 900 days.

(21) Appl. No.: 10/589,692

(22) PCT Filed: Feb. 18, 2005

(86) PCT No.: PCT/EP2005/050728

§ 371 (c)(1),
(2), (4) Date: Aug. 17, 2006

(87) PCT Pub. No.: WO2005/080990

PCT Pub. Date: Sep. 1, 2005

(65) Prior Publication Data

US 2007/0196878 A1    Aug. 23, 2007

(30) Foreign Application Priority Data

Feb. 19, 2004 (IT) ............................ RM2004A0091

(51) Int. Cl.
*A61K 39/04* (2006.01)
(52) U.S. Cl. .............. 424/248.1; 424/185.1; 424/190.1; 435/975; 530/300; 530/350
(58) Field of Classification Search ........................ None
See application file for complete search history.

(56) References Cited

FOREIGN PATENT DOCUMENTS

| WO | 98/16646 | 4/1998 |
|---|---|---|
| WO | 99/04005 | 1/1999 |
| WO | 00/26248 | 5/2000 |
| WO | 02/054072 | 7/2002 |
| WO | 2004/005925 | 1/2004 |

OTHER PUBLICATIONS

Andersen, "TB Vaccines: Progress and Problems," Trends Immunol. 22:160-168, 2001.
Cockle et al., "Identification of Novel Mycobacterium Tuberculosis Antigens with Potential as Diagnostic Reagents or Subunit Vaccine Candidates by Comparative Genomics," Infect. Immun. 70:6996-7003, 2002.
Pinxteren et al., "Diagnosis of Tuberculosis Based on the Two Specific Antigens ESAT-6 and CFP10," Clin. Diagn. Lab. Immunol. 7:155-160, 2000.
International Search Report from PCT/EP2005/050728.
International Preliminary Report on Patentability from PCT/EP2005/050728.

*Primary Examiner*—Jennifer E Graser
(74) *Attorney, Agent, or Firm*—Clark & Elbing LLP

(57) ABSTRACT

The present invention relates to a method of diagnosing and monitoring various distinct presentations of tuberculosis: active tuberculosis disease, latent tuberculosis infection and recent tuberculosis infection. The rapid immune assay is based on the evaluation of the frequency of Interferon (IFN) gamma-producing antigen-specific T lymphocytes responding to selected peptide sequences from *Mycobacterium tuberculosis*, selected for their immunogenicity. The invention concerns also immunogenic and vaccine compositions based on these specific peptide sequences.

4 Claims, 10 Drawing Sheets

Response to pool of selected peptides

CTR

TB

IMMUNE DIAGNOSTIC ASSAY TO DIAGNOSE AND MONITOR TUBERCULOSIS INFECTION

CROSS-REFERENCE TO RELATED APPLICATIONS

This application claims priority under 35 U.S.C. §371 from international application PCT/EP2005/050728, filed Feb. 18, 2005, which claims priority from Italian Patent Application RM2004A000091, filed Feb. 19, 2004.

FIELD OF INVENTION

The present invention relates to a method of diagnosing and monitoring various distinct presentations of tuberculosis: active tuberculosis disease, latent tuberculosis infection and recent tuberculosis infection. The rapid immune assay is based on the evaluation of the production of Interferon (IFN) gamma by antigen-specific T lymphocytes responding to selected peptide sequences from secretory proteins of *Mycobacterium tuberculosis*. These peptide sequences have been selected for their immunogenicity. The test may be performed by ELISPOT, ELISA or FACS techniques and the eventual choice of methodology to carry out the test is done according to the resources and the requirements of the laboratory.

DEFINITIONS

In the present invention, by using the following terms, we indicate by:
"virulent *M. tuberculosis*" a bacterium capable of causing the tuberculosis disease in a mammal including a human being.
"patient with tuberculosis infection" either a) an individual with a recent or old contact with tuberculosis and in these cases it is not possible to culture virulent *M. tuberculosis*; b) an individual with culture proven infection with virulent *M. tuberculosis*.
"patient with latent tuberculosis infection" an individual with an old contact with tuberculosis. It is not possible to culture virulent *M. tuberculosis*.
"patient with active tuberculosis or with tuberculosis disease" an individual with culture proven infection with virulent *M. tuberculosis*. Culture diagnosis of tuberculosis is well known by the person skilled in the art
"tuberculosis contact", an individual exposed to patients with active pulmonary tuberculosis, sputum positive
"tuberculosis complex", the complex of mycobacteria causing tuberculosis which are *M. tuberculosis, M. bovis, M. Bovis* BCG, and *M. africanum*.
"health care worker", and individual working in the health system with patients with different disease
Sensitivity of a test for active tuberculosis: Percentage of positive responses of a test over the whole number of samples tested from patients with a microbiologically confirmed active tuberculosis
Specificity of a test for active tuberculosis: Percentage of negative responses of a test over the whole number of samples tested from patients without microbiologically confirmed active tuberculosis
RD1 genome: Section of genome encoding ESAT-6 and CFP-10 proteins and specific for *M. tuberculosis* and absent in Bacillus Calmette and Guerin used for vaccine
RD1 proteins/peptides: In this invention by RD1 peptides and proteins we include only ESAT-6 and CFP-10 proteins and derived peptides
TST: turbeculin skin test. This test involves measurement of increase in skin inflammation site (for example diameter of circular swelling and redness) 72 hours after intradermal injection of mycobacterial extracts termed purified protein derivatives (PPD)
Absolute value: Numerical value of response from output [for example spot forming cells (SFCs) for ELISPOT*, which is calibrated by subtracting the control (Reagent 1 & Sample) numerical value from the test output (Reagent 2-5/2-7 & Sample) numerical value

BACKGROUND

Approximately 3 million tuberculosis-related deaths occur in the world annually and it is estimated that one third of the world's population is infected with *M. tuberculosis* (MTB) (Dye et al 1999). The rapid and accurate detection of the infection is crucial for the global control of the disease. At present, the diagnosis of active tuberculosis disease, and therefore the subsequent evaluation of the efficacy of anti-tuberculosis treatment, are based on the time-consuming microbiological culture of *M. tuberculosis* (that has 85% sensitivity), with a turnaround time of 26 weeks. This molecular diagnostic techniques proved to be useful only for culture-positive samples (American Thoracic Society 1997), and are available in highly specialized laboratories only. Therefore tuberculosis remains a global health problem because of the long time needed for microbiological diagnosis and because of the difficulty in monitoring the efficacy of anti-tuberculosis therapy. In the field, the tuberculin skin test (TST) is presently used to support the diagnosis of tuberculosis in patients without microbiological confirmation of the disease (Fine et al 1999, Huebner et al 1993, American Thoracic Society 2000, CDC MMWR Recommendation and Reports 1997). However, this test has significant limitations as purified protein derivative (PPD) used for TST is a crude precipitate of filtered MTB containing more than 200 antigens widely shared among environmental mycobacteria (Fine et al 1999, Huebner et al 1993, American Thoracic Society 2000. CDC MMWR Recommendation and Reports 1997). In patients with tuberculosis, the TST is 75-90% sensitive, but among those with disseminated disease, this sensitivity falls to 50% (Fine et al 1999, Huebner et al 1993, American Thoracic Society 2000). It is even lower in HIV+ patients with only mild degrees of immunosuppression (Fine et al 1999, Huebner et al 1993, American Thoracic Society 2000, CDC MMWR Recommendation and Reports 1997). Moreover, a positive TST does not discriminate between latent and active tuberculosis and thus, in subjects with a positive test, further clinical work is needed to obtain a correct diagnosis (Fine et al 1999, Huebner et al 1993).

From the immunological point of view, it has been demonstrated that *M. tuberculosis* evokes a strong cell-mediated immune response in vitro, with a high production of interferon (IFN)-gamma. The detection of T cells secreting this cytokine in response to *M. tuberculosis* antigens represents a tool to diagnose infection (Andersen et al 1993).

Recent studies have led to the identification of the genomic segment RD1, present In the *M. tuberculosis* complex but absent from *M. bovis* of BCG (*Bacillus* Calmette and Guerin), which is currently used as a vaccine and from the majority of environmental mycobacteria (Mahairas et al 1996, Harboe et al 1996, WO 2004/099771, EP 1 350 839 A: van Pinxteren 2000; Cockle 2002; Andersen 2001; WO 99/04005; WO 99/42076 A; WO 97/09428 A; WO 01/04151 A; WO 01/79274 A; WO 03/093307 A). RD1 encodes the Earty Secretory Antigenic Target (ESAT)-6 and the Culture Filtrate Protein (CFP)-10. These proteins, synthesized by the bacterium during the active replication phase, are dominant targets for cell-mediated immunity in animal models (Andersen et al 1995, Pollock et al 1997, WO 2004/099771, WO 00/26248 A; EP 1 350 839 A: van Pinxteren 2000; Cockle 2002; Andersen 2001; WO 99/04005; WO 99/42076 A; WO 97/09428 A; WO 01104151 A; WO 01/79274 A; WO 03/093307 A) and in patients with tuberculosis (Ulrichs et al 1998, Ravn et al 1999. WO 00/26248 A) and subjects exposed to M. tuberculosis who develop the disease within 2 years (Doherty et al 2002). For these reasons, the response of peripheral blood mononuclear cells (PBMC) to ESAT-6 or CFP-10 proteins (Lalvani et al 2001-a, 2001-b, and 2001-c, Pathan et al 2001) has been correlated with tuberculosis diagnosis by using the IFN-gamma ELISPOT assay. This technique allows estimating the frequency of T cells that are producing a given cytokine (for example, IFN-gamma) in response to a specific antigenic stimulus, for example ESAT-6, CFP-10, PPD (Purified Protein Derivative), etc. The response to the whole ESAT-8 or CFP-10 proteins allows discrimination between BCG-vaccinated subjects and subjects infected with M. tuberculosis. In fact, only the subjects who have been exposed to M. tuberculosis, either BCG-vaccinated or not, display an in vitro response to these proteins that are absent from M. bovis and BCG. In line with these studies two commercial tests (QuantiFERON-TB Gold—Cellestis Limited, Carnagie, Victoria, Australia and the T SPOT-TB, Oxford Immunotec, Oxford, UK) (Pai et al 2004, Mori et al 2004) were developed. Both tests evaluate cell mediated immune response to M. tuberculosis by measuring IFN-gamma released from T cells in response to M. tuberculosis antigens, using methods such as ELISA and ELISPOT respectively. In both assays M. tuberculosis antigens consist in ESAT-6 and CFP-10 overlapping peptides spanning the whole proteins. These assays appear to provide a quite accurate diagnosis of tuberculosis infection. However, such response does not allow discriminating between subjects with active tuberculosis and subjects with latent infection.

Thus, as in the case of a positivity to TST, a positive response to these immune tests based on RD1 overlapping peptides require further clinical workup to rule out an active tuberculosis. This example is particular relevant considering a subject with a suspect of active tuberculosis (thus with clinical symptoms of active disease) resulting positive to these conventional tuberculosis assays because with a latent TB infection (Richeldi et al, 2004a&b; Ravn, 2004; Brock, 2004). These results can lead to an incorrect diagnosis, because the subject may have a disease that mimics active tuberculosis, but different from tuberculosis (such as a bacterial pneumonia, a viral fever, a bronchitis) and thus he may start an incorrect treatment, he may be isolated from the community if the suspect is a pulmonary tuberculosis, with relevant human and economic costs.

Thus the distinction between active and latent tuberculosis is important to:
a) provide a correct diagnosis, because the active form of the disease leads to organ destruction and/or death and to the spread of infection the community; in contrast the latent infection does not involve organ destruction and it is not dangerous for the community
b) provide a correct and efficacious therapy, because active tuberculosis requires regime of first 2 months therapy with 4 drugs and then followed by 4 months therapy with 2 drugs, whereas for latent tuberculosis it is necessary to treat the patient with one drug for 6 months
c) save human and economic costs avoiding complex evaluations (i.e. clinical, radiological and surgery procedures).

Our assay is different because first of all, we may discriminate between active and latent tuberculosis compared to other patent applications and scientific articles (US2004058399; WO02059605; WO0104151; WO0026248; WO9221097; WO 2004/099771, EP 1 350 839 A; van Pinxteren 2000; Cockle 2002; Andersen 2001; WO 99/04005; WO 99/42076 A; WO 97/09428 A; WO 01/04151 A; WO 01/79274 A: WO 03/093307 A). In addition we may monitor the therapy efficacy or failure in a more accurate way. In fact having set up a cut-off, in the case of therapy efficacy, the selected peptides response goes under the detection level, differently from others in which it is mentioned only a vaguely decrease of the response (Lalvani et al, 2001b; (US2004058399; WO 2004/099771, EP 1 350 839 A; van Pinxteren 2000; Cockle 2002; Andersen 2001; WO 99/04005; WO 99142076 A; WO 97/09428 A; WO 01/04151 A; WO 01/79274 A; WO 03/093307 A).

The possibility to monitor therapy efficacy by our assay is particularly relevant because it is:
a) easy to perform by a simple blood draw instead of a invasive surgery procedures;
b) unexpensive, compared to the surgery procedures involved in a biopsy, if an extra-pulmonary tuberculosis is suspected, or a broncoscopy, if the patient is sputum negative
c) more accurate compared to the assays based on RD1 overlapping peptide because our assay may distinguish between active and latent tuberculosis while the other immune assays are associated to tuberculosis infection (see below).

SUMMARY OF THE INVENTION

The novelty of our assay is the use of specifically selected CFP-10 peptides separately (FIG. 1A) and in combination with ESAT-6 specifically selected peptides (Vincenti et al 2003). As seen in FIG. 1B among patents with microbiologically confirmed active tuberculosis, the use of selected peptides from CFP-10 leads to a higher sensitivity of the assay compared to the use of only ESAT-6 selected peptides. In FIG. 1B it is also noticeable that the combination of ESAT-6 and CFP-10 has the highest sensitivity for active tuberculosis. Overtapping ESAT-6 and CFP-10 peptides were used in the previous patent applications and scientific articles (WO0026248; US2004058399; WO 20041099771, EP 1 350 839 A; van Pinxteren 2000; Cockle 2002; Andersen 2001; WO 99/04005; WO 99/42076 A: WO 97/09428 A; WO 01/04151 A; WO 01/79274 A; WO 03/093307 A). In addition we report that these selected peptides may be used with different experimental methods to achieve the same result: such as ELISPOT assay, FACS analysis and whole blood ELISA. In addition, in the present invention we used a rapid method to separate circulating mononuclear cells in the blood sample (LeucoSep, ARNIKA, Milan, Italy) which is different from what has been used in other patents (for example Par. 18 of EP1152012). This method, compared to traditional methods, allows processing several samples at once.

This assay employs a rapid method for the detection of:

a) frequency of IFN-gamma-producing T lymphocytes in response to RD1 selected peptides and intact proteins identified by the ELISPOT technique on peripheral blood mononuclear cells b) quantitative response of T lymphocytes to RD1 selected peptides and intact proteins in terms of IFN-gamma production, evaluated by the ELISA technique, performed on plasma samples after stimulation of whole blood with specific antigens (Ag)

c) frequency of IFN-gamma-producing T lymphocytes in response to RD1 selected peptides and intact proteins identified by flow cytometric analysis (FACS) on peripheral blood mononuclear cells (PBMC)

The diagnostic test according to the present invention, is performed on peripheral venous blood or on mononuclear cells obtained from peripheral venous blood. It is composed of a reagent kit which can be designed to cater different situations under which the diagnosis might take place, and requires the availability of an ELISPOT or ELISA reader, or a flow cytometer, for the evaluation of results. The detailed description of the invention will highlight further objects.

DETAILED DESCRIPTION

The selection and use of our CFP-10 peptides (Table 1) is novel compared to what is reported in the literature resulting in a higher potency of immunogenicity. This selection has been performed by computational analysis by the use of special software (Rammensee et al 1999, Fleckenstein et al 1999, Stumiolo et al 1999, 1997) in order to cover more than 90% of the HLA-class II haplotypes present in the human population.

The sequences were selected on a random mapping of small peptide sequences and selected for their promiscuousity as T-cell epitopes. The reason behind the strength of these selected sequences remains elusive at the moment. The response to these peptides, in terms of IFN-gamma production evaluated by ELISPOT or whole blood ELISA or FACS, is associated to active tuberculosis.

TABLE 1

| Protein | Position | Nucleotide sequence and corresponding amino acid sequence |
|---|---|---|
| CFP-10 | 18-31 | SEQ ID NO: 1<br>TTCGAGCGGATCTCCGGCGACCTGAAAACCCAGA<br>TCGACCAG<br>SEQ ID NO: 2<br>FERISGDLKTQIDQ |
| CFP-10 | 41-68 | SEQ ID NO: 3<br>GGCCAGTGGCGCGGCGCGGCGGGGACGGCCGCCC<br>AGGCCGCGGTGGTGCGCTTCCAAGAAGCAGCCAA<br>TAAGCAGAAGCAGGAA<br>SEQ ID NO: 4<br>GQWRGAAGTAAQAAVVRFQEAANKQKQE |
| CFP-10 | 53-68 | SEQ ID NO: 5<br>GCCGCGGTGGTGCGCTTCCAAGAAGCAGCCAATA<br>AGCAGAAGCAGGAA<br>SEQ ID NO: 6<br>AAVVRFQEAANKQKQE |
| CFP-10 | 74-86 | SEQ ID NO: 7<br>ACGAATATTCGTCAGGCCGGCGTCCAATACTCGA<br>GGGCC<br>SEQ ID NO: 8<br>TNIRQAGVQYSRA |

Figure 1A:
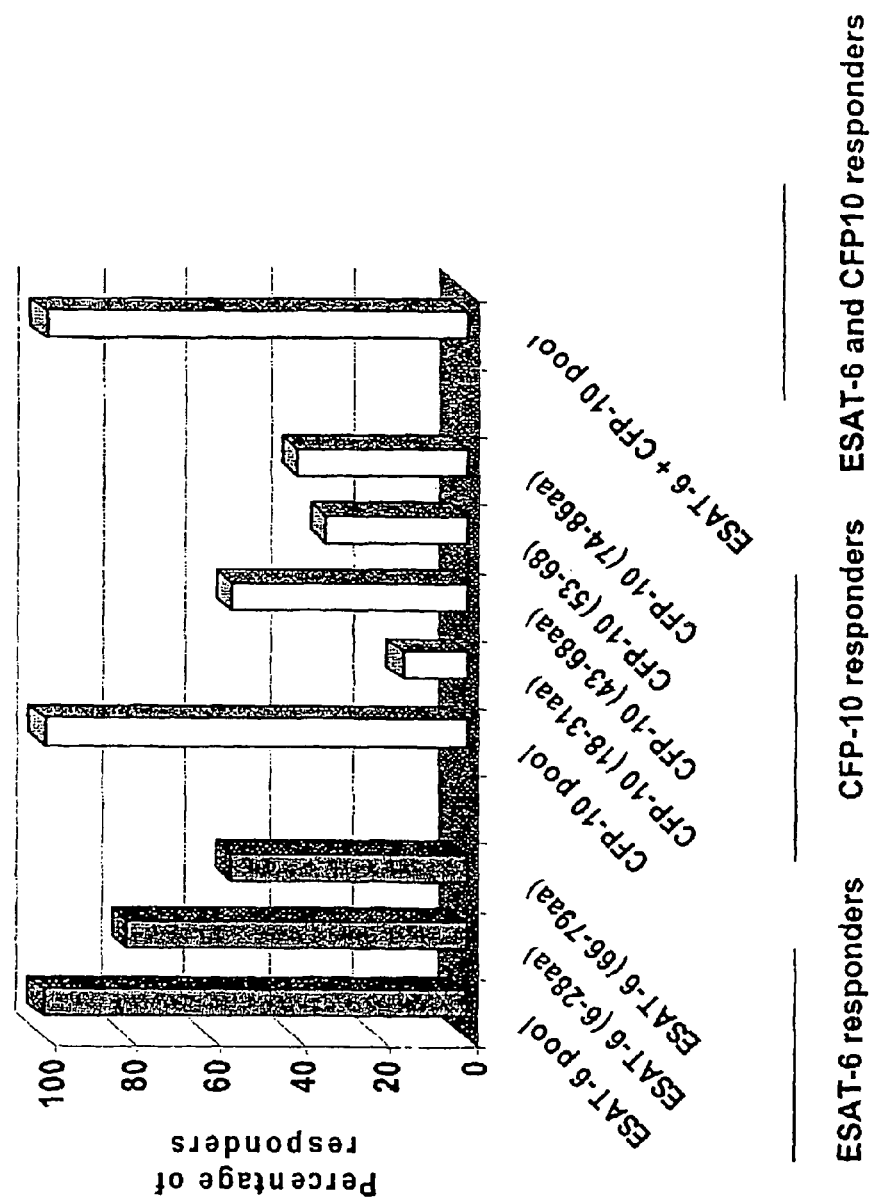
FIG. 1A, Percentage of patients with active tuberculosis responding to the single or pooled selected peptides among those with a positive response to ESAT-6 or CFP-10 pool by ELISPOT assay.
Figure 1B:
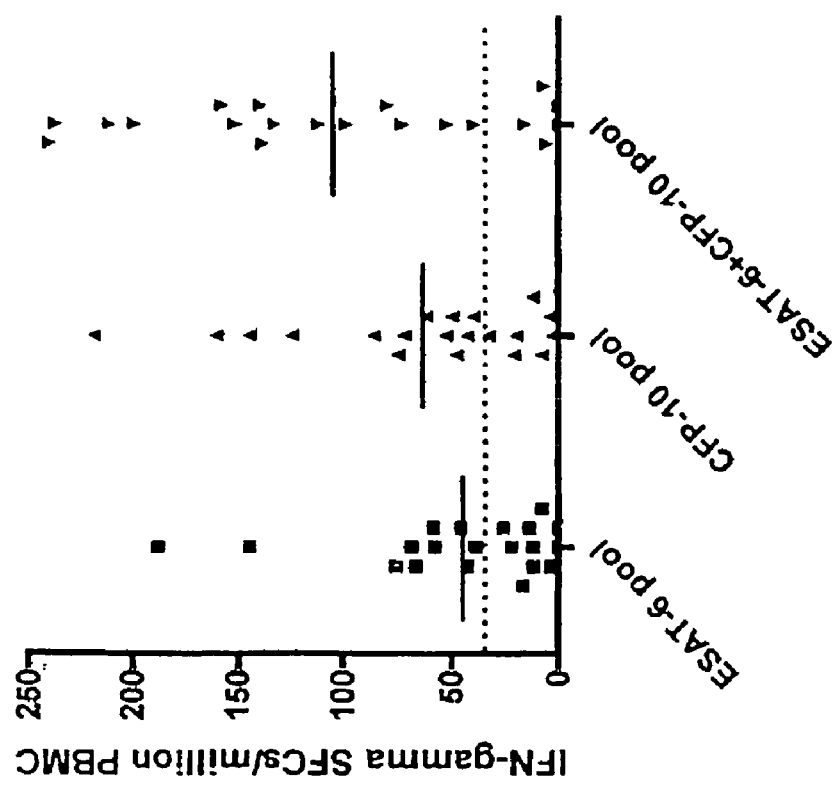
FIG. 1B. IFN-gamma response to RD1 peptides pool in patients with active tuberculosis. Detection of IFN-gamma was performed by ELISPOT assay. For each patient with active tuberculosis the highest response to either ESAT-6 peptide pool or CFP-10 peptide pool or ESAT-6+CFP-10 peptide pool specific IFN-gamma secreting T cells, is reported as spot forming cell (SFC). Horizontal bars represent the mean of the SFC for each group.

Realising the potential of the discovery at hand, the test was modified and improved in order to increase its sensitivity and feasibility. In addition the potential of the kit was tested on the monitoring of the outcome of anti-tuberculosis treatment. Also, it was tested that the combination of CFP-10 selected peptides with 2 peptides selected from ESAT-6, which is another specific protein of M. tuberculosis (Table 2), increases the sensitivity of the assay. In fact ESAT-6 selected peptides, by themselves, are less sensitive in the assay than CFP-10 selected peptides, but together have a higher sensitivity (FIG. 1B).

TABLE 2

| Protein | Position | Nucleotide sequence and corresponding amino acid sequence |
|---|---|---|
| ESAT-6 | 6-28 | SEQ ID NO: 9<br>TGGAATTTCGCGGGTATCGAGGCCGCGGCAAGCG<br>CAATCCAGGGAAATGTCACGTCCATTCATTCCCT<br>C<br>SEQ ID NO: 10<br>WNFAGIEAAASAIQGNVTSIHSL |
| ESAT-6 | 67-79 | SEQ ID NO: 11<br>AACGCGCTGCAGAACCTGGCGCGGACGATCAGCG<br>AAGCC<br>SEQ ID NO: 12<br>NALQNLARTISEA |

The in vitro immune diagnostic assay for tuberculosis diagnosis, according to the invention, is performed using a diagnostic kit comprising at least one CFP-10 peptide selected among the group of SEQ ID NO 2, SEQ ID NO 4, SEQ ID NO 6, SEQ ID NO 8, and corresponding mixtures. It is preferable to use a mixture containing at least one of the above-specified peptides and at least one ESAT-6 peptide chosen from the group of SEQ ID NO 10, SEQ ID NO 12 and corresponding mixtures. The sequences are then called as reagents 3-5, as detailed in the list below:

Reagent 1: CTR, complete culture medium or medium comprising the solvent concentration present in Reagents 3-5; the solvent preferred is the dimethyl sulfoxide (DMSO)

Reagent 2. at least one intact protein selected between ESAT-6 and CFP-10, or preferably a mixture of them. For example the product of Lionex, Braunschweig. Germany for both CFP-10 and ESAT-6 or Statens Serum Institut, Copenhagen, Denmark for ESAT-6;

Reagent 3: at least one ESAT-6 peptide selected in the group of SEQ ID NO 10, 12. or preferably a mixtures thereof, diluted in DMSO as described above Reagent 4: at least one CFP-10 peptide selected in the group of SEQ 10 NO 2, 4, 6, 8, or preferably a mixtures thereof, diluted in DMSO as described above;

Reagent 5: a mixture of at least one ESAT-6 and one CFP-10 peptides selected in the group of SEQ ID NO 2, 4, 6, 8, 10, 12, diluted in DMSO as described above, or preferably a mixture of all of them, Reagent 6: a T cell positive stimulus; a possible stimulus is (PHA) phytohemagglutinin, Reagent 7: (PPD) Purified Protein Derivative, for example the product of Statens Serum Institut, Copenhagen, Denmark.

These reagents would form part of a complete diagnostic kit. It is worthwhile to note that reagent 2 is also used. Its presence increases the information regarding the status of tuberculosis. To achieve the results required, the following fundamental steps should be carried out. The details of the precise methodology are variable but would remain obvious to persons skilled in the art:

admix an aliquot of venous blood or mononuclear cells (PBMC) obtained from venous blood with each stimulus:

incubate at 37° C. as long as necessary according to the method used, either ELISPOT, FACS, or whole blood ELISA.

To evaluate the responses the following protocols of procedure have to be carried out. The choice of protocol depends on the answer one is looking to answer from the test:

1) by a "basic protocol" (using Reagents 1-5) it is possible to discriminate among: active tuberculosis patients, patients with recent tuberculosis infection (contact), latent tuberculosis subjects, healthy subjects unexposed to M. tuberculosis. It is also possible to monitor the efficacy of anti-tuberculosis treatment (e.g. to distinguish in subjects TST-positive in a context of MTB exposure whether these subjects are with latent TB or re-infected with MTB, then the "basic protocol" would be advisable)

2) by a "complete protocol" (using Reagents 1-7), in addition to what above described, it is possible to distinguish between: anergic individual, BCG-vaccinated/exposed to atypical mycobacteria individual. (e.g. to distinguish in subjects TST-positive in a context of MTB exposure whether these subjects are BCG-vaccinated or MTB-infected, then the complete protocol would be advisable):

In both protocols, when evaluating by whole blood ELISA, the blood sample will be placed into heparinised test tubes; when by ELISPOT assay or FACS analysis EDTA-containing tubes will be used for the blood drawing.

PBMC can be well isolated by density gradient centrifugation using a rapid method based on the use of special tubes equipped with a filter for leukocyte separation; an expert in the field is able to choose the best procedure and is also familiar with ELISA and ELISPOT and FACS methods.

In the case of ELISPOT, PBMC obtained from whole blood are incubated for approximately 40 hours (range: 38-40 hours), and the outcome is a quantitative determination of IFN-gamma production by antigen-specific T lymphocytes. Amount of blood required 5 ml.

In the case of ELISA, whole blood is incubated for approximately 24 hours, and the outcome is a quantitative determination of IFN-gamma production by antigen-specific T lymphocytes, as indicated below. Amount of blood required 2-5 ml.

In the case of FACS, PBMC are incubated for approximately 16 hours (range: 14-16 hours) and the outcome is a qualitative (presence/absence of antigen-specific T lymphocytes) and quantitative determination (percentage and frequency of specific cells per $mm^3$ of blood), as indicated below. Amount of blood required 5 ml.

We briefly describe the experimental section regarding the execution of ELISPOT, whole blood ELISA, and FACS techniques. However, by reading the teachings of the invention and using his knowledge, the expert in the field is able to select the suitable conditions (in terms of concentration, times, temperatures, etc.) to perform the assay according to the invention. When running an experiment by the ELISPOT assay (FIG. 2), mononuclear cells (PBMC) are isolated as described in detail in the literature (Lalvani et at 2001-a). The cells are then treated with the selected peptides, [(preferably the 2 ESAT-6 pooled peptides at 50 µg/mL (25 µg/mL each), the 4 CFP-10 pooled peptides at 8 µg/mL (2 µg/mL each), and a mixture of the RD1 peptides at 60 µg/mL)], with purified protein derivative (PPD) (batch RT47; Statens Serum Institut, Copenhagen, Denmark) at 10 µg/mL, with phytohemagglutinin (PHA) (Sigma, St Louis, Mo., USA) at 1 µg/mL, with RD1 proteins (Lionex; Braunschweig, Germany) at a concentration of 2 µg/mL each. Negative controls included PBMC, either unstimulated or treated with DMSO, at the same concentration present in the peptide solutions. Circulating specific T-cells are evaluated by the ELISPOT method as described in detail in the literature (Lalvani et al 2000-a). Spots are counted automatically by an ELISA-Spot assay video analysis system (AELVIS, Hannover, Germany).

If the experiment is carried out on whole blood (FIG. 3), the selected peptides and the other Reagents are added directly to the blood. Reagents' concentrations are the following: the selected peptides, preferably the 2 ESAT-6 pooled peptides at 50 µg/mL (25 µg/mL each), the 4 CFP-10 pooled peptides at 8 µg/mL (2 µg/mL each), and a mixture of the RD1 peptides at 5 µg/mL), purified protein derivative (PPD) (batch RT47; Statens Serum Institut, Copenhagen, Denmark) at 5 µg/ml. phytohemagglutinin (PHA) (Sigma, St Louis, Mo., USA) at 1 µg/mL, RD1 proteins (Lionex, Braunschweig, Germany) at a concentration of 0.2 µg/mL each. Plasma is collected after 24 hr of incubation at 37° C. and tested for the presence of IFN-gamma by ELISA. Results are then read by the use of an ELISA reader.

If the experiment is carried out by FACS analysis (FIG. 4), the PBMC, isolated as described above, are stimulated with the reagents at the same concentration used for ELISPOT, with the exception of RD1 proteins that are used at 5 µg/mL each. The results are then acquired and analysed using a flow cytometer.

Flow Chart of the Results Scoring.

At the beginning of the data analysis the results obtained by the stimulation with the reagents R2-7 are put in relation with the correspondent cut-off values found by constructing a receiver operator characteristic (ROC) curve analysis. In particular the results of the assay are evaluated on the basis of the absolute value calculated by the subtraction of the value obtained in control wells (whole blood or PBMC with only Reagent 1) from that in stimulated wells (samples with Reagents 2-7). By ROC analysis, we found a cut-off minimums for e.g. ELISPOT and ELISA assays:

ELISPOT: 34 spots (per million PBMC) for Reagents 3-5: 36 spots (per million PBMC) for Reagents 2; 60 spots (per million PBMC) for Reagents 6, 7
ELISA: 0.6 IU/ml for Reagents 2-7

If the absolute value of the reagents R2-7 is below the correspondent cut-off value the output is correspondently not valid. If the absolute value of the reagents R2-7 is above the correspondent cutoff value the following criteria should be fulfilled.

Positive Criteria for the "Basic Protocol":

the response to Reagent 2 (row number) is at least 3-fold higher than that to Reagent 1 when the CTR comprises medium;

the response to Reagent 3 (row number) is at least 2-fold higher than that to Reagent 1 when the CTR comprises the DMSO at the same concentration present in the Reagent 3;

the response to Reagents 4 (row number) is at least 4-fold higher than that to Reagent 1 when the CTR comprises the DMSO at the same concentration present in the Reagent 4 the response to Reagents 5 (row number) is at least 4-fold higher than Reagent 1 when the CTR comprises the DMSO at the same concentration of the Reagent 5.

Positive Criteria for the "Complete Protocol":

the responses to Reagents 6 and 7 (row number) are at least 3-fold higher than that to Reagent 1 when the CTR comprises medium.

The following table summarises the interpretation of a positive result for various outcomes. Notice how Reagent 2 by itself (without Reagent 3+4+5) cannot differentiate between active and latent tuberculosis patients response to selected peptides of ESAT-6 or selected CFP-10 peptides or a pool of CFP-10 & ESAT-6 peptides).

(iii). BCG-vaccinated healthy subjects: positive response due to contact of PBMC sample or whole blood with single Reagents 6-7 (negative response to RD1 both intact proteins and selected peptides).

(iv). healthy subjects unvaccinated and unexposed to *M. tuberculosis*: positive response due to contact of PBMC sample or whole blood with Reagent 6 only (negative response to PPD, and to RD1 both intact proteins and selected peptides).

(v). anergic subjects: negative response after contact of PBMC sample or whole blood with single reagents, including Reagent 6 which is a mitogen able to induce a response in all subjects with an efficient immune system.

(vi). Monitoring the efficacy of anti-tuberculosis treatment and the replication phase of the *M. tuberculosis* after recent disease. At the time of active disease diagnosis or in the case of a recent infection, the PBMC or whole blood samples respond to reagents 2-5 in the "basic protocol" and 2-7 in the "complete protocol" as described in point (i). On the contrary, after 3 months of effective therapy (no active *M. tuberculosis* replication), the PBMC or whole blood samples respond to Reagents 2, 6, 7 only (absence of a significant response to RD1 peptides), as described in point (ii)

(vii) survey of tuberculosis in HIV-infected patients based on the previous points (i-vi)

(viii) survey of tuberculosis in children based on the previous points (i-vi)

(ix) survey of tuberculosis infection in health care workers based on the previous points (i-vi); in addition the peptide response [as indicated in (i)] correlates with TST size.

The method and the kit can be used for diagnosing active tuberculosis disease, for diagnosing a recent infection in

TABLE 3

| | | | | |
|---|---|---|---|---|
| "Complete protocol": Reagents 1*-7 | | | | |
| | "Basic protocol": Reagents 1*-5 | | | |
| PHA Reagent 5 | PPD Reagent 7 | RD1 PROTEINS Reagent 2 | RD1 PEPTIDES Reagents 3 + 4 + 5 | STATUS |
| − | − | − | − | Anergic |
| + | − | − | − | Healthy subject |
| + | + | − | − | BCG-vaccinated or exposed to atypical mycbacteria |
| + | + | + | − | Latent TB or TB patient under efficacious anti-TB therapy |
| + | + | + | + | Active TB or recent TB infection or TB re-infection |

*Reagent 1: CTR, complete culture medium or medium comprising the dimethyl sulfoxide (DMSO) concentration present in Reagents 3-7. Criteria of scoring the results as negative and positive are indicated in the text Interpretation Criteria of the Results (i). patients with active disease or patients with recent tuberculosis Infection (contacts) (active replication of *M. tuberculosis*): in the "basic protocol" positive response due to contact of PBMC or whole blood with single Reagents 2 (intact proteins of CFP-10 and ESAT-6), Reagents 3+4+5 (selected peptides of ESAT-6 or CFP-10 or a pool of CFP-10 & ESAT-8 peptides) and in the "complete protocol" positive response also to Reagents 6-7 with (PHA and PPD).

(ii). patients with latent infection (no active replication of *M. tuberculosis*): positive response due to contact of PBMC or whole blood samples with single Reagents 2, 6, 7 (negative healthy contacts of a patient with a sputum-positive pulmonary tuberculosis, for monitoring the response to treatment in the case of pulmonary and extra-pulmonary tuberculosis and to discriminate between latent and active tuberculosis disease state.

To define the status of the patient, it is necessary to quantify the output of the responses (output is, for example for ELISPOT, the number of SFCs) As explained above, the absolute value is determined by subtracting the control output to from the row number. Scoring procedures are then performed as indicated above. The results are then analyzed to determine the status of tuberculosis as explained in Table 3.

Figure 9:
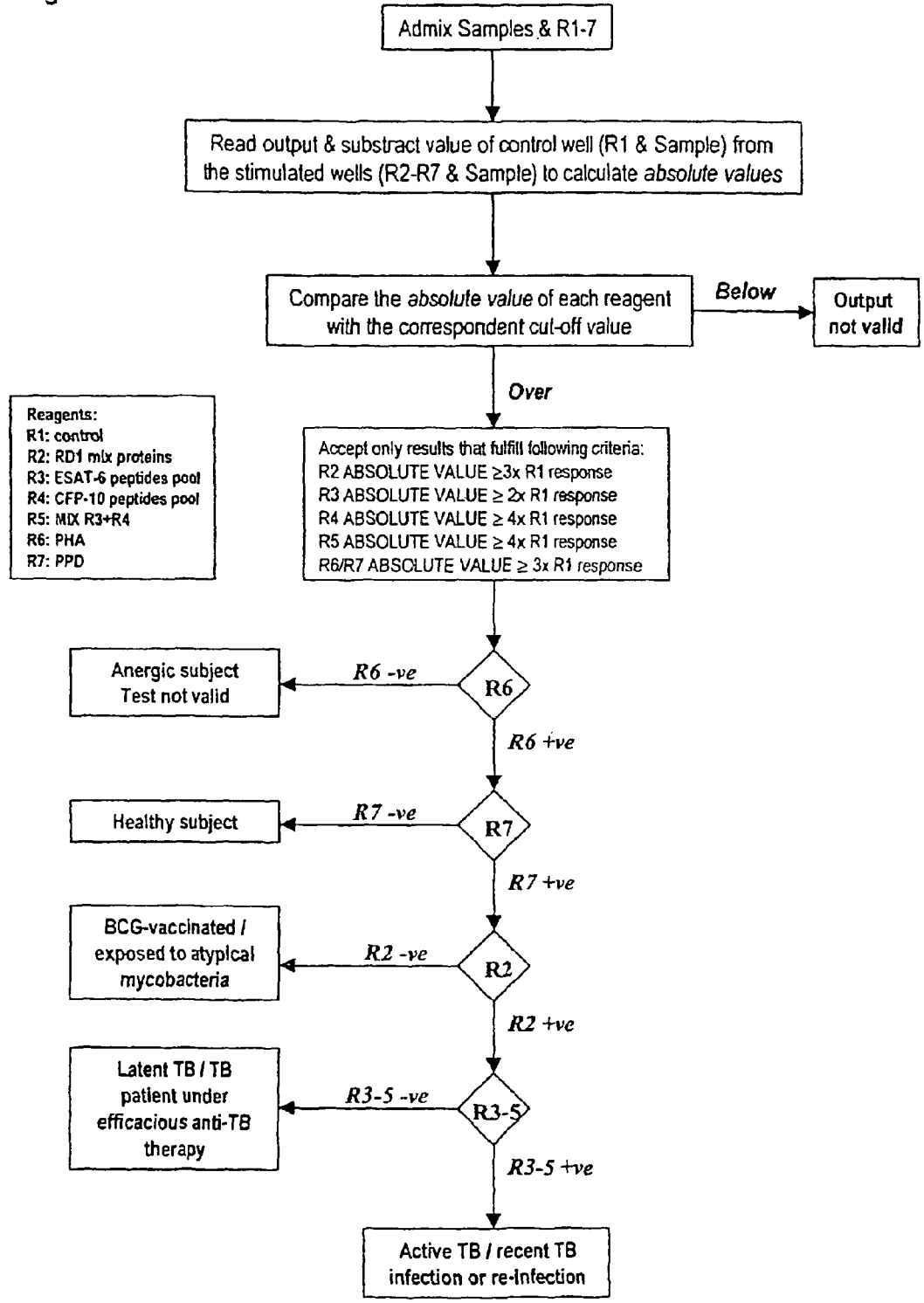
FIG. 9. Flow chart showing the logic behind any application of the present method in order to analyze the results

Such a process is highly suited to a computer program and the logic behind any such software is represented in FIG. 9

The method and the kit according to the invention are generally performed on samples from an individual who is preferably a human, but may be an animal (typically an animal which can be naturally or artificially infected by the relevant pathogen, i.e. a laboratory animal), Thus the individual may be a mammal, such as a primate, cow, sheep, pig, badger or rodent, e.g. a mouse or rat.

Moreover the test according to the invention can be performed by determining other cytokines, such as TNF-alpha, GMSF, interleukins 1-24.

The present invention can be advantageously implemented through a program for computer comprising program coding means for the implementation of one or more steps of the method, when this program is running on a computer. Therefore, it is understood that the scope of protection is extended to such a program for computer and in addition to a computer readable means having a recorded message therein, said computer readable means comprising program coding means for the implementation of one or more steps of the method, when this program is run on a computer.

The response to the RD1 selected peptides is due to the activation of CD4+T lymphocytes.

The scientific basis of the assay according to the present invention is grounded on our epidemiological studies and corresponding statistic evaluation of data, collected according to the following.

Figure 2:
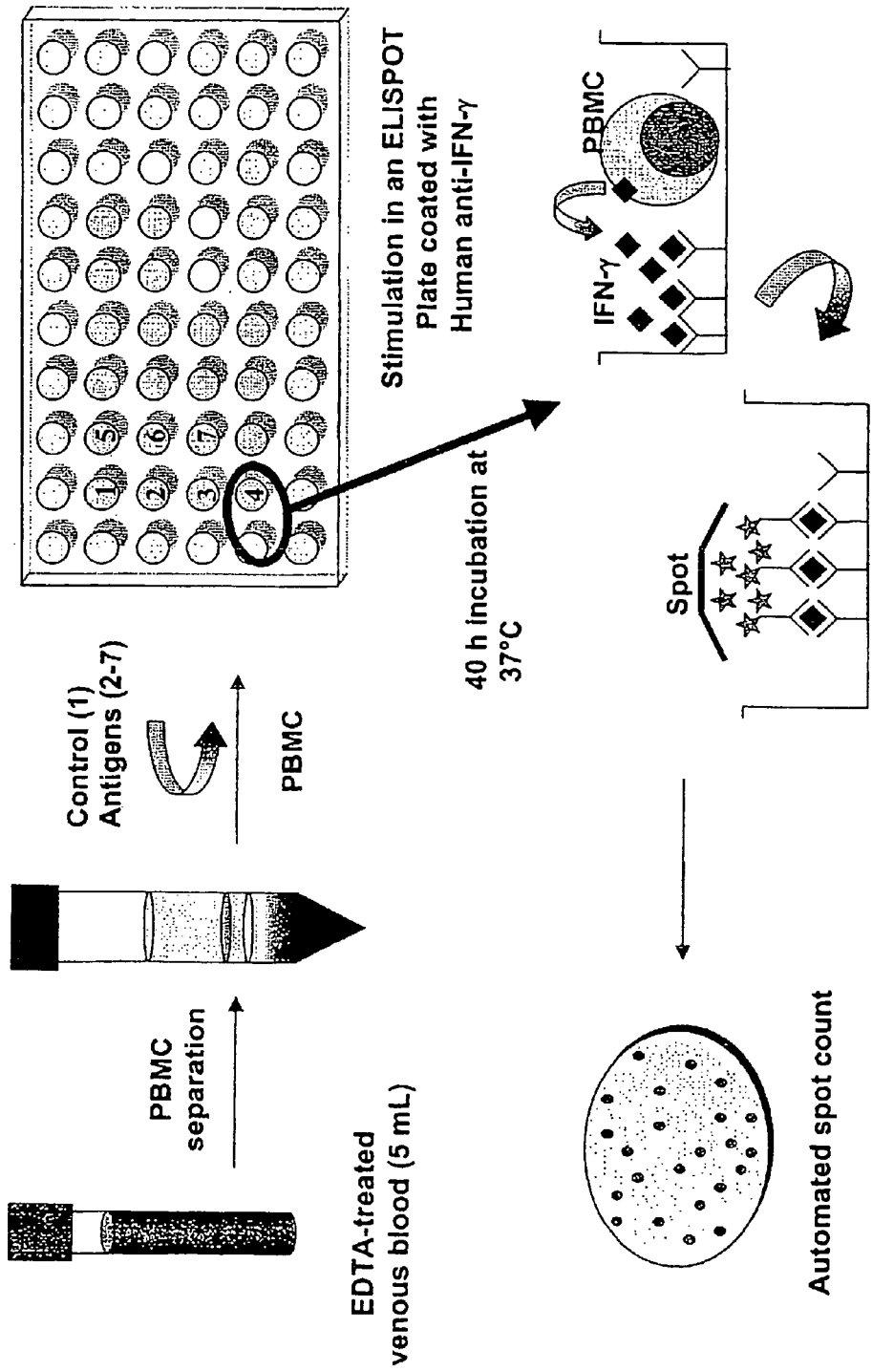
FIG. 2. ELISPOT test procedure.

Example of the Procedure of the ELISPOT-Based Immune Diagnostic Assay (see FIG. 2)

The whole procedure of the test requires the use of the following reagents and materials: 96-well plate (MAIPS45, Millipore, Sunnyvale, Calif., USA); primary antibody (IFN-gamma coating monoclonal, M-700A, Pierce-Endogen Inc, Rockford, Ill., USA); biotin-labelled antibody (M-701B. Pierce-Endogen Inc): streptavidin-HRP (Pierce-Endogen); AEC substrate (AEC Staining kit, Sigma); 7 tubes, each containing the different stimuli at the desired concentration.

The ELISPOT Method is Composed of the Following Steps:

Coating 1. coat the 96-well plate by distributing 100 μL/well of a solution of the primary antibody diluted in sterile phosphate-buffered saline (PBS) at a concentration of 5 μg/mL
2. cover the plate and incubate at 4° C. for 20 hours
3. wash the plate 4 times with 200 μL/well sterile PBS; after the last wash, remove excess liquid by gently tapping the plate on blotting paper Blocking 1. add 200 μL/well of "blocking solution" [sterile PBS containing 10% fetal bovine sum (FBS)], to prevent unspecific binding of proteins
2. incubate the plate for 2 hours at room temperature
3. aspirate blocking solution Preparation and Incubation of Cells 1. isolate mononuclear cells (PBMC) from venous blood (5 mL with EDTA) by rapid density gradient centrifugation (Ficoll-Hypaque, Pharmacia; Uppsala; Sweden), using filter-equipped tubes for leukocyte separation (LeucoSep™, ARNIKA, Milan, Italy). After two washes with 1×PBS (phosphate buffered saline), the pellet is resuspended in the complete medium (RPMI 1640 supplemented with 25 mM HEPES, 10% v/v FBS, 2 mM L-Glutamine, 10 U/mL penicillin/streptomycin) to a final concentration of $2.5 \times 10^5$ cells in 110 μL.

2. add 110 μL of cell suspension to the wells, together with 110 μL of the different stimuli according to the scheme in table 4.
3. incubate the plate for 40 hours at 37° C. in a 5% $CO_2$ incubator
4. remove the cells
5. wash the plate 4 times with 200 μL/well PBS and 4 times with 200 μL/well "Wash buffer" [PBS/0.05% Tween 20 (Sigma)]
6. after the last wash remove excess liquid by gently tapping the plate on blotting paper Incubation with Biotin-Labelled Antibody 1. distribute 100 μL/well of biotin-labelled antibody dissolved in PBS/4% bovine serum albumin (fraction V, Sigma) at a concentration of 1 μg/mL
2. incubate for 100 minutes at 37° C. in a 5% $CO_2$ incubator
3. wash the plate 4 times with "Wash buffer"
4. after the last wash, remove excess liquid by gently tapping the plate on blotting paper Development 1. distribute 100 μL/well "Streptavidin-HRP" diluted 1:1000 in "Wash buffer"
2. incubate for 30 minutes at room temperature in the dark
3. wash plate 4 times with "Wash buffer"
4. after the last wash, remove excess liquid by gently tapping the plate on blotting paper
5. add 100 μL/well of AEC substrate. Check that enzyme-substrate reaction takes place by incubating 100 μL of the freshly made substrate solution with 100 μL of the "Streptavidin-HRP" solution. If the reaction occurs the substrate turns from a light brown colour to pink.
6. incubate 10-20 minutes at room temperature in the dark
7. discard the substrate, rinse the plate with running water, remove excess liquid and allow the plate to dry for 20 hours

TABLE 4

| Reagent | Stimulus and working concentration (values in parentheses relate to concentration in μg/mL) | Concentration of stock solution (mg/mL) | Volume to be added (μL) |
| --- | --- | --- | --- |
| 1 | CTR* or DMSO** (8) or DMSO** (60) | ** | 110 |
| 2 | ESAT-6 protein (2) and CFP-10 protein (2) | 0.004 | 110 |
| 3 | Pool of ESAT-6 peptides (50) | 0.1 | 110 |
| 4 | Pool of CFP-10 peptides (8) | 0.016 | 110 |
| 5 | Pool of ESAT-6 and CFP-10 peptides (58) | 0.12 | 110 |
| 6 | PHA (1) | 0.02 | 110 |
| 7 | PPD (10) | 0.02 | 110 |

*CTR: complete culture medium
**for DMSO: an identical solvent concentration will be added in reagent 1 corresponding to the amount of DMSO present in reagents 3-5.

Evaluation of Results and Diagnostic Response

Spot Count

Spots are counted automatically by an automated ELISA-spot assay video analysis system (A.EL.VIS. Hannover, Germany).

Responses were scored as positive when the average number of spots in wells stimulated with:

a) PHA, PPD, ESAT-6 and CFP-10 proteins: is at least 3-fold higher than the number of spots in corresponding control wells that contained unstimulated cells only b) pool of CFP-10 selected peptides: is at least 4-fold higher than the number of spots in corresponding control wells, containing DMSO at the same concentration used to dilute the peptides c) pool of ESAT-6 selected peptides: is at least 2-fold higher than the number of spots in corresponding control wells containing DMSO at the same concentration used to dilute the peptides d) mixture of the pools of RD1 selected peptides: was at least 4-fold higher than the number of spots corresponding control wells containing DMSO at the same concentration used to dilute the peptides In addition, if the number of spots in a stimulated well was less than or equal to 10, the response was scored as negative.

To obtain the absolute value, the number of spots in control wells was subtracted from the number of spots in simulated wells. Using LABROC-1 software, a Receiver Operator Characteristic (ROC) curve was constructed to obtain a specific cut-off value for every stimulus in our study population.

Evaluation of Test Results

1a) Active tuberculosis, Recent Tuberculosis Infection (Contact), Monitoring of the Response to Anti-*Tuberculosis Therapy Over Time*

T0: time of diagnosis of active tuberculosis disease or of recent tuberculosis infection. ELISPOT test is performed on PBMC. Table 5 shows the mean values of duplicate wells obtained by counting spots using the automated reader:

TABLE 5

| Reagent | Stimulus and working concentration (values in parentheses relate to concentration in μg/mL) | SFCs**/2.5 × 10$^5$ cells) |
|---|---|---|
| 1 | CTR* or DMSO (8) or DMSO (60) | 3 or 5 or 6 |
| 2 | ESAT-6 protein (2) and CFP-10 protein (2) | 195 |
| 3 | Pool of ESAT-6 peptides (50) | 101 |
| 4 | Pool of CFP-10 peptides (8) | 125 |
| 5 | Pool of ESAT-6 and CFP-10 peptides (58) | 130 |
| 6 | PHA (1) | 240 |
| 7 | PPD (10) | 180 |

*CTR: complete culture medium
**SFCs: Spot Forming Cells

The absolute value is obtained by subtracting the number of spots in control wells from the number of spots in corresponding stimulated wells, as shown in the following table (table 6):

According to the test, the sample is an active tuberculosis (or a recent infection, depending on clinical, radiological and microbiological context) since there is a positive response not only to proteins, but also to RD1 peptide pools as happens specifically during active tuberculosis. In fact, the average number of spots in wells stimulated with a) PHA, PPD, ESAT-6 and CFP-10 proteins: is at least 3-fold higher than the number of spots in corresponding control wells, that contained unstimulated cells only b) pool of selected CFP-10 peptides: is at least 4-fold higher than the number of spots present in corresponding control wells that contained the same DMSO concentration used to dilute the peptides c) pool of selected ESAT-6 peptides: is at least 2-fold higher than the number of spots present in corresponding control wells that contained the same DMSO concentration used to dilute the peptides d) mixture of the RD1 selected peptide pools: is at least 4-fold higher than the number of spots present in corresponding control wells that contained the same DMSO concentration used to dilute the peptides The obtained values were also above the cut-off calculated for each stimulus.

T1: 3 months after commencement of anti-tuberculosis treatment or 3 months after diagnosis of recent tuberculosis infection (contact).

In the case of active tuberculosis the ELISPOT test is repeated after 3 months to verify the efficacy of anti-tuberculosis therapy. If the patient responded well to pharmacological therapy, test results of RD1 intact proteins remain positive (latent tuberculosis, see following example, 1b), but those of the tuberculosis specific selected peptide pools become negative.

In the case of a recent infection, the patient was recalled 3 months after his contact with the proven sputum-positive tuberculosis case to repeat the TST, and on the occasion the ELISPOT test was performed again. If the patients did not develop the disease, having contained the infection, test results will show positive responses to RD1 intact proteins, as described above, (latent tuberculosis, see following example, 1b), and negative responses to the pools of selected peptides, that are specific for active tuberculosis.

1b) Latent Tuberculosis

Table 7 shows the mean values of duplicate wells obtained by counting spots using an automated reader.

TABLE 6

| Stimulus and working concentration (values in parentheses relate to concentration in μg/mL) | SFCs/2.5 × 10$^5$ cells | Corresponding control | SFCs/2.5 × 10$^5$ cells | Absolute value |
|---|---|---|---|---|
| ESAT-6 protein (2) and CFP-10 protein (2) | 195 | CTR | 3 | 192 |
| ESAT-6 pooled peptides (50) | 101 | DMSO (60) | 6 | 95 |
| CFP-10 pooled peptides (8) | 125 | DMSO (8) | 5 | 120 |
| ESAT-6 and CFP-10 pooled peptides (58) | 130 | DMSO (60) | 6 | 124 |
| PHA (1) | 240 | CTR | 3 | 237 |
| PPD (10) | 180 | CTR | 3 | 177 |

TABLE 7

| Reagent | Stimulus and working concentration (values in parentheses relate to concentration in µg/mL) | SFCs**/2.5 × 10$^5$ cells |
|---|---|---|
| 1 | CTR* or DMSO (8) or DMSO (60) | 4 or 3 or 5 |
| 2 | ESAT-6 protein (2) and CFP-10 protein (2) | 195 |
| 3 | Pool of ESAT-6 peptides (50) | 6 |
| 4 | Pool of CFP-10 peptides (8) | 7 |
| 5 | Pool of ESAT-6 and CFP-10 peptides (58) | 9 |
| 6 | PHA (1) | 240 |
| 7 | PPD (10) | 180 |

*CTR: complete culture medium
**SFCs: Spot Forming Cells

The absolute value is obtained by subtracting the number of spots in control wells from the number of spots in stimulated wells, as shown in the following table (table 8):

TABLE 8

| Stimulus and working concentration (values in parentheses relate to concentration in µg/mL) | SFCs/2.5 × 10$^5$ cells | Corresponding control | SFCs/2.5 × 10$^5$ cells | Absolute value |
|---|---|---|---|---|
| ESAT-6 protein (2) and CFP-10 protein (2) | 195 | CTR | 5 | 191 |
| Pool of ESAT-6 peptides (50) | 6 | DMSO (60) | 5 | 1 |
| Pool of CFP-10 peptides (8) | 7 | DMSO (8) | 3 | 4 |
| Pool of ESAT-6 and CFP-10 peptides (58) | 9 | DMSO (60) | 5 | 4 |
| PHA (1) | 240 | CTR | 4 | 236 |
| PPD (10) | 180 | CTR | 4 | 176 |

According to the test, the sample is a latent tuberculosis since the response to proteins is positive, but the response to the RD1 peptide pools is negative. In fact, the average number of spots in wells stimulated with a) PHA, PPD, ESAT-6 and CFP-10 proteins: is at least 3-fold higher than the number of spots present in corresponding control wells b) pool of CFP-10 selected peptides: is not 4-fold higher than the number of spots present in corresponding control wells that contained the same DMSO concentration used to dilute the peptides c) pool of ESAT-6 selected peptides: is at least 2-fold higher than the number of spots in corresponding control wells that contained the same DMSO concentration used to dilute the peptides.

d) mixture of the RD1 selected peptide pools: is not 4-fold higher than the number of spots in corresponding control wells that contained the same DMSO concentration used to dilute the peptides The obtained values were also above the cutoff for all stimuli, with the exception of the pool of RD1 selected peptides.

Patients were enrolled at T0 because of a suspected active tuberculosis disease or because they were healthy contacts of patients with active sputum-positive MTB, nevertheless test results for some of them were negative (latent tuberculosis cases or controls), or unevaluable (anergy). Consequently, these patients will not be reevaluated after 3 months (T1).

1c) BCG-Vaccinated Healthy Control

Table 9 shows average values in duplicate wells, obtained by counting spots using an automated reader:

TABLE 9

| Reagent | Stimulus and working concentration (values in parentheses relate to concentration in µg/mL) | SFCs**/2.5 × 10$^5$ cells |
|---|---|---|
| 1 | CTR* or DMSO (8) or DMSO (60) | 3 |
| 2 | ESAT-6 protein (2) and CFP-10 protein (2) | 7 |
| 3 | Pool of ESAT-6 peptides (50) | 6 |
| 4 | Pool of CFP-10 peptides (8) | 5 |
| 5 | Pool of ESAT-6 and CFP-10 peptides (58) | 5 |
| 6 | PHA (1) | 240 |
| 7 | PPD (10) | 155 |

*CTR: complete culture medium
**SFCs: Spot Forming Cells

The absolute value is obtained by subtracting the number of spots in control wells from the number of spots in stimulated wells, as shown in the following table (table 10).

TABLE 10

| Stimulus and working concentration (values in parentheses relate to concentration in µg/mL) | SFCs/2.5 × 10⁵ cells | Corresponding control | SFCs/2.5 × 10⁵ cells | Absolute value |
|---|---|---|---|---|
| ESAT-6 protein (2) and CFP-10 protein (2) | 7 | CTR | 3 | 4 |
| Pool of ESAT-6 peptides (50) | 6 | DMSO (60) | 3 | 3 |
| Pool of CFP-10 peptides (8) | 5 | DMSO (8) | 3 | 2 |
| Pool of ESAT-6 and CFP-10 peptides (58) | 5 | DMSO (60) | 3 | 2 |
| PHA (1) | 240 | CTR | 3 | 237 |
| PPD (10) | 155 | CTR | 3 | 152 |

According to the test, the sample is a BCG-vaccinated healthy control since the response to PHA and PPD is positive but the response to both RD1 proteins and peptide pools is negative. In fact the average number of spots in wells stimulated with a) PHA, PPD: is at least 3-fold higher than the number of spots in control wells that contained unstimulated cells only b) ESAT-6 and CFP-10 proteins: is not 3-fold higher than the number of spots in control wells that contained unstimulated cells only c) pool of CFP-10 selected peptides: is not 4-fold higher than the number of spots In corresponding control wells that contained the same DMSO concentration used to dilute the peptides d) pool of ESAT-6 selected peptides: is not 2-fold higher than the number of spots in corresponding control wells that contained the same DMSO concentration used to dilute the peptides e) mixture of the RD1 selected peptide pools: is not 4-fold higher than the number of spots in corresponding control wells that contained the same DMSO concentration used to dilute the peptides.

In addition, only the results obtained with PHA and PPD are above the cut-off value.

1d) Healthy Control (BCG-Unvaccinated, Unexposed to *M. tuberculosis*)

Table 11 shows mean values of duplicate wells obtained by counting spots using an automated reader:

TABLE 11

| Reagent | Stimulus and working concentration (values in parentheses relate to concentration in µg/mL) | SFCs**/2.5 × 10⁵ cells |
|---|---|---|
| 1 | CTR* or DMSO (8) or DMSO (60) | 3 or 2 r 6 |
| 2 | ESAT-6 protein (2) and CFP-10 protein (2) | 5 |
| 3 | Pool of ESAT-6 peptides (50) | 6 |
| 4 | Pool of CFP-10 peptides (8) | 5 |
| 5 | Pool of ESAT-6 and CFP-10 peptides (58) | 8 |
| 6 | PHA (1) | 240 |
| 7 | PPD (10) | 6 |

*CTR: complete culture medium
**SFCs: Spot Forming Cells

The absolute number is obtained by subtracting the number of spots in control wells from the number of spots in stimulated wells, as shown in the following table (table 12)

TABLE 12

| Stimulus and working concentration (values in parentheses relate to concentration in µg/mL) | SFCs/2.5 × 10⁵ cells | Corresponding control | SFCs/2.5 × 10⁵ cells | Absolute value |
|---|---|---|---|---|
| ESAT-6 protein (2) and CFP-10 protein (2) | 5 | CTR | 3 | 2 |
| ESAT-6 pooled peptides (50) | 6 | DMSO (60) | 6 | 0 |
| CFP-10 pooled peptides (8) | 5 | DMSO (8) | 2 | 3 |
| Pool of ESAT-6 and CFP-10 peptides (58) | 8 | DMSO (60) | 6 | 2 |
| PHA (1) | 240 | CTR | 3 | 237 |
| PPD (10) | 6 | CTR | 3 | 3 |

According to the test, the sample is a healthy control since the response to PHA only is positive, while responses to PPD, RD1 proteins and peptide pools are negative. In fact, the average number of spots in wells stimulated with a) PHA: is at least 3-fold higher than the number of spots in corresponding control wells that contained un-stimulated cells only b) PPD, ESAT-6 and CFP-10 proteins: is not 3-fold higher than the number of spots in corresponding that contained un-stimulated cells only c) pool of CFP-10 selected peptides: is not 4-fold higher than the number of spots in corresponding control wells that contained the same DMSO concentration used to dilute the peptides d) pool of ESAT-6 selected peptides: is not 4-fold higher than the number of spots in corresponding control wells that contained the same DMSO concentration used to dilute the peptides.

e) mixture of the RD1 selected peptide pools: is not 4-fold higher than the number of spots in corresponding control wells that contained DMSO at the same concentration used to dilute the peptides In addition, only PHA results are above the cut-off value.

1e) Anergy

Table 13 shows average values obtained by counting spots using an automated reader:

TABLE 13

| Reagent | Stimulus and working concentration (values in parentheses relate to concentration in µg/mL) | SFCs**/ $2.5 \times 10^5$ cells |
|---|---|---|
| 1 | CTR* or DMSO (8) or DMSO (60) | 5 |
| 2 | ESAT-6 protein (2) and CFP-10 protein (2) | 5 |
| 3 | ESAT-6 pooled peptides (50) | 6 |
| 4 | CFP-10 pooled peptides (8) | 5 |
| 5 | Pool of ESAT-6 and CFP-10 peptides (58) | 3 |
| 6 | PHA (1) | 11 |
| 7 | PPD (10) | 6 |

*CTR: complete culture medium
**SFCs: Spot Forming Cells

The absolute value is obtained by subtracting the number of spots in control wells from the number of spots in stimulated wells as shown in the following table (table 14):

TABLE 14

| Stimulus and working concentration (values in parentheses relate to concentration In µg/mL) | SFCs/ $2.5 \times 10^5$ cells | Corresponding control | SFCs/ $2.5 \times 10^5$ cells | Absolute value |
|---|---|---|---|---|
| ESAT-6 protein (2) and CFP-10 protein (2) | 5 | CTR | 5 | 0 |
| ESAT-6 pooled peptides (50) | 6 | DMSO (60) | 5 | 1 |
| CFP-10 pooled peptides (8) | 5 | DMSO (8) | 5 | 0 |
| ESAT-6 and CFP-10 pooled peptides (58) | 3 | DMSO (60) | 5 | 0 |
| PHA (1) | 11 | CTR | 5 | 6 |
| PPD (10) | 6 | CTR | 5 | 1 |

According to the test, the sample is that of an anergic subject, since even the response to PHA, which is a mitogen, is negative. In fact, the average number of spots In wells stimulated with a) PHA, PPD and ESAT-6 and CFP-10 proteins: is not 3-fold higher than the number of spots in corresponding control wells that contained unstimulated cells only b) pool of CFP-10 selected peptides: is not 4-fold higher than the number of spots in corresponding control wells that contained the same DMSO concentration used to dilute the peptides c) pool of ESAT-6 selected peptides: is not 2-fold the number of spots present in corresponding control wells that contained the same DMSO concentration used to dilute the peptides d) mixture of RD1 selected peptide pools: is not 4-fold higher than the number of spots in corresponding control wells that contained the same DMSO concentration used to dilute the peptides.

In addition, the obtained results are all below the cut-off value.

EXAMPLE 2

Figure 3:
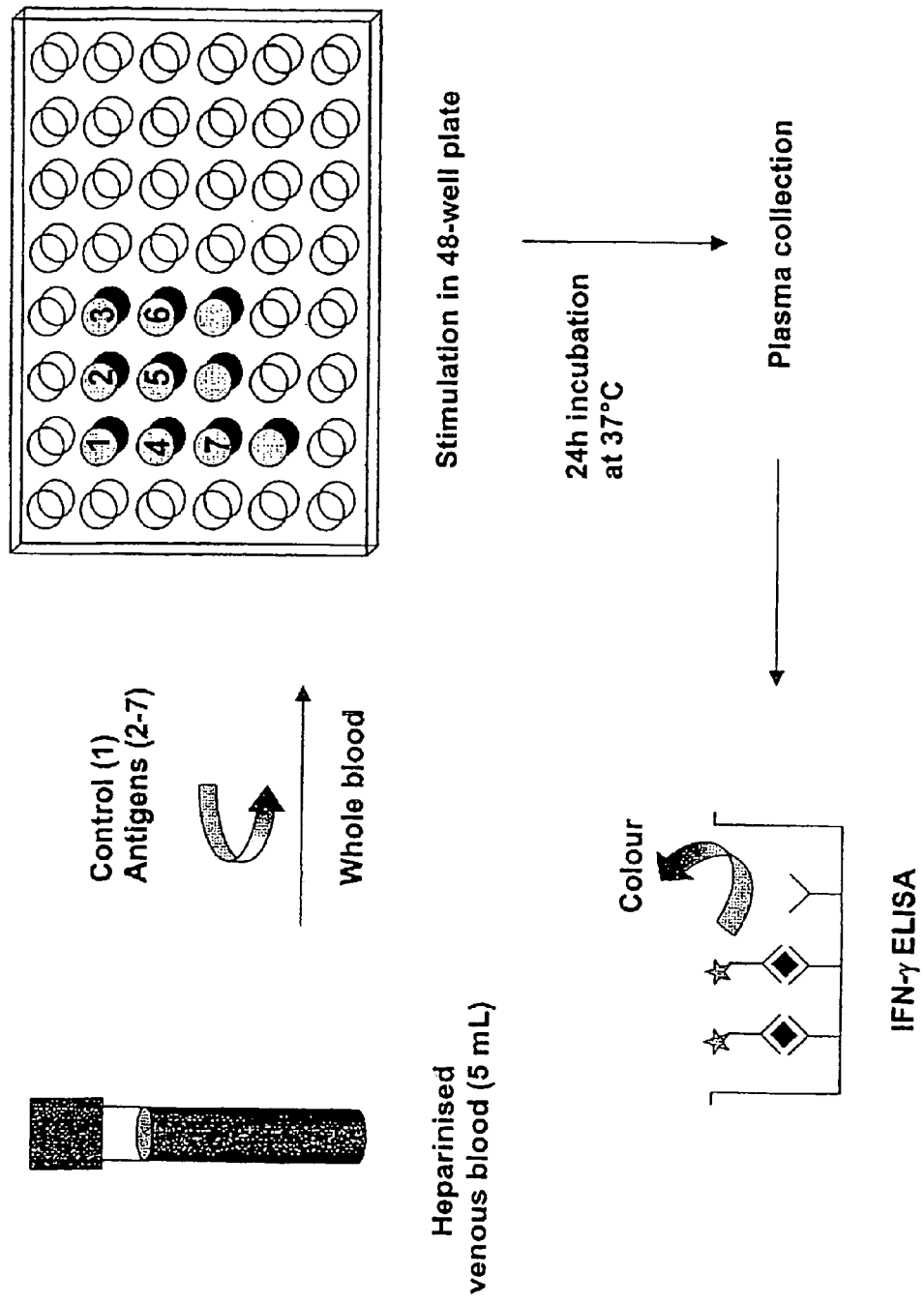
FIG. 3. Whole blood ELISA test procedure.

Procedure of the Immune Diagnostic Assay Performed on Whole Blood by ELISA See FIG. 3

The ELISA method on whole blood is performed by the use of the QuantiFERON-CMI (QF-CMI, manufactured by Cellestis Limited. South Melbourne, Australia), modified by us. In detail, we use 0.5 ml of blood instead of 1 ml, and therefore we use a 48-well plate instead of a 24-well. The whole procedure of the test requires the use of the following materials and reagents: IFN-gamma QuantiFERON-CMI kit; 48-well plate and 7 tubes, each containing the different stimuli at the desired concentration. The ELISA technique, performed on whole blood, is composed of the following steps:

1. Culture of Whole Blood 1. mix the tubes containing heparinised whole blood 2. distribute blood (500 µl/well) into sterile 48-well plates. For the children similar results can be obtained using 250 µl/well of blood. Consequently the volume of the Reagents 1-7 to be added will be 50% of the volume indicated.

3. add control mitogen and specific antigens according to the scheme in table 15

4. mix well 5. incubate plate at 37° C. for 24 hours 6. harvest plasma aliquots from each well

TABLE 15

| Reagent | Stimulus and working concentration (values in parentheses relate to concentration in µg/mL) | Concentration of stock solution for 0.5 ml of blood (mg/mL) | Volume to be added (µL) |
|---|---|---|---|
| 1 | CTR* or DMSO (8)**, or DMSO (60)** | ** | 50 |
| 2 | ESAT-6 protein (0.2) and CFP-10 protein (0.2) | 0.01 | 50 |
| 3 | ESAT-6 pooled peptides (50) | 0.5 | 50 |
| 4 | CFP-10 pooled peptides (8) | 0.08 | 50 |
| 5 | ESAT-6 and CFP-10 pooled | 0.6 | 50 |

TABLE 15-continued

| Reagent | Stimulus and working concentration (values in parentheses relate to concentration in µg/mL) | Concentration of stock solution for 0.5 ml of blood (mg/mL) | Volume to be added (µL) |
|---|---|---|---|
| | peptides (58) | | |
| 6 | PHA (1) | 0.05 | 50 |
| 7 | PPD (5) | 0.05 | 50 |

*CTR: complete culture medium
**for DMSO: an identical solvent concentration will be added in reagent 1 corresponding to the amount of DMSO present in reagents 3-5.

Step 2. IFN-gamma-based ELISA 1. prepare "conjugated antibody" by dissolving it in the "green diluent" solution, and distribute in the ready-to-use ELISA plate.

2. add harvested plasma and "standard solution" to the corresponding wells containing "green diluent"

3. mix well 4. cover the plate and incubate for 2 hours at room temperature 5. wash with "wash buffer"

6. prepare the 100× "chromogen" by diluting it with the "enzyme substrate buffer" and distribute in the plate 7. cover the plate and incubate for 30 minutes at room temperature in the dark 8. add stop solution to block the reaction and immediately read optic density in each well, at 450/620 nm using an ELISA reader.

Evaluation of Test Results and Diagnostic Response

The optic density values of the plate are analysed, a standard curve and IFN-gamma values, expressed as International Units (I.U.)/mL, are calculated for each well by the use of special software provided by the manufacturer.

This method, as the previously described ones, allows identification of the different types of patients: active tuberculosis patients; patients with recent tuberculosis infection (contacts); latent tuberculosis patients; BCG-vaccinated healthy controls; healthy controls unvaccinated and unexposed to MTB; anergic patients. Monitoring of the efficacy of anti-tuberculosis treatment is also possible using this method.

For example, a subject with active tuberculosis will display positive results not only to RD1 proteins, but also to their pooled peptides.

IFN-gamma concentration (I.U/mL) in wells stimulated with a) PHA, PPD, ESAT-6 and CFP-10 proteins: is at least 3-fold higher than that in corresponding control wells that contained unstimulated cells only b) pool of CFP-10 selected peptides: is at least 4-fold higher than that of corresponding control wells that contained the same DMSO concentration used to dilute the peptides c) pool of ESAT-6 selected peptides: is at least 2-fold higher than that in corresponding control wells that contained the same DMSO concentration used to dilute the peptides.

e) mixture of the RD1 selected peptide pools: is at least 4-fold higher than that in corresponding control wells that contained the same DMSO concentration used to dilute the peptides. In addition, based on the ROC analysis a cut-off has been found: 0.6 IU ml for Reagents 2-7. To score the results follow instructions at the "scoring result section" above and follow the examples reported in EXAMPLE 1.

EXAMPLE 3

Procedure of the Immune Diagnostic Assay Performed by FACS

Figure 4:
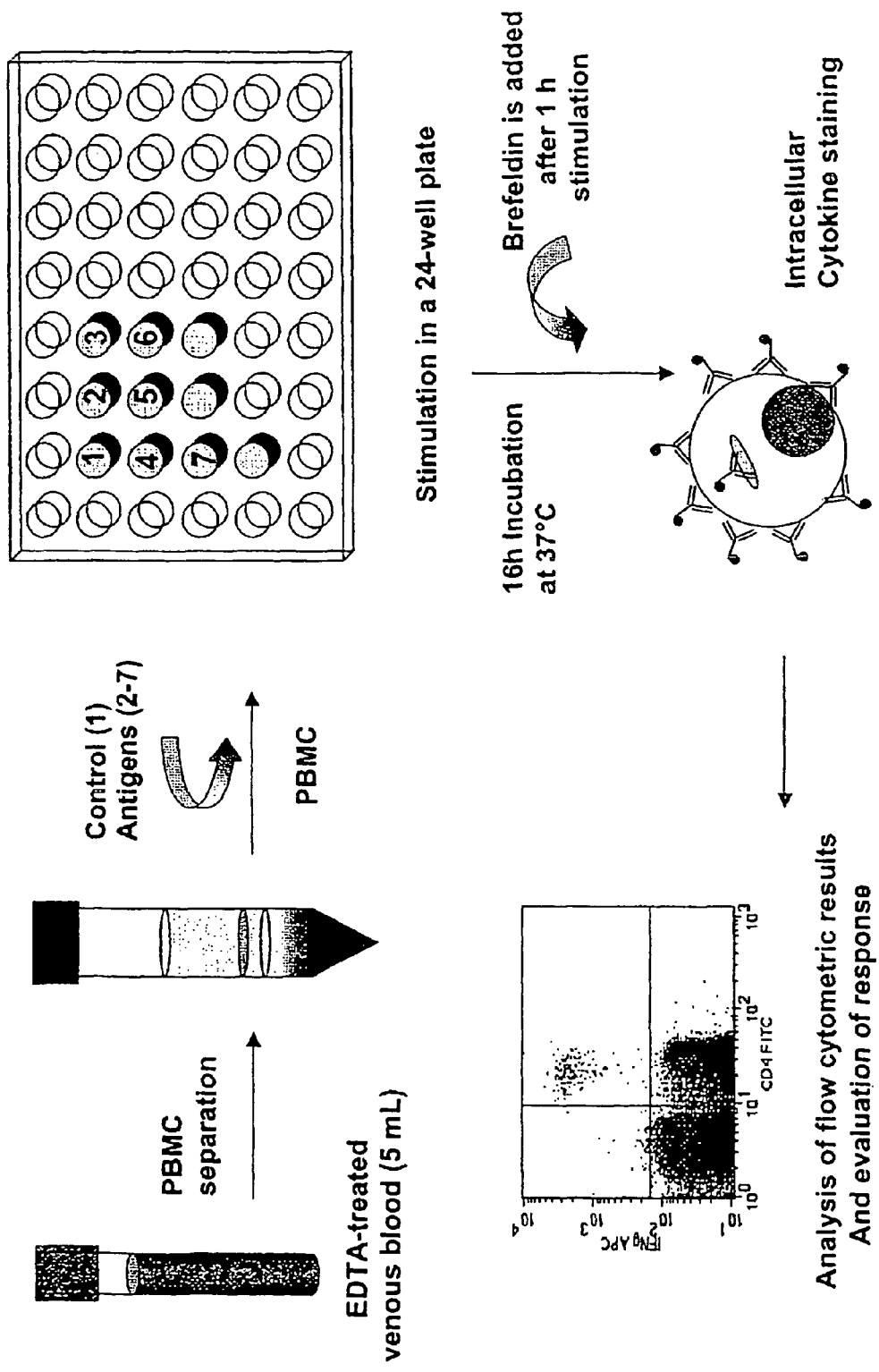
FIG. 4. FACS analysis procedure.

See FIG. 4

The whole procedure of the test requires the use of an IFN-gamma flow cytometer and the following materials and reagents: 24-well plate; mixture of antibodies (Becton-Dickinson, CA); brefeldin-A (Sigma, St. Louis, Mo.) and 7 tubes, each containing the different stimuli at the desired concentration.

In particular the FACS analysis method is composed of the following steps:

i. isolation of mononuclear cells (PBMC) from venous blood ii. stimulation of Ag-Sp and incubation iii. immunofluorescence staining iv. acquisition and FACS analysis v. diagnostic response.

In step (i), peripheral blood mononuclear cells (PBMC) are isolated from a small aliquot of venous blood (5 ml) by density gradient centrifugation (Ficoll-Hypaque, Pharmacia; Uppsala; Sweden) using a rapid test based on the use of special tubes equipped with a filter for the separation of leukocytes (LeucoSep™, ARNIKA, Milan. Italy). After 2 washed with 1×PBS (phosphate buffered saline), the cell pellet is resuspended in the complete medium (RPMI 1640 with 25 mM HEPES, 10% v/v FBS, 2 mM L-Glutamine, 10 U/mL penicillin/streptomycin) to a cell concentration of $1 \times 10^6$ cells in 500 µL.

In step (ii), PBMC are seeded (500 µL/well) in a 24-well plate with the mitogen and the antigen-specific (Ag-Sp) solutions, according to the scheme in table 21. PBMC are thus incubated at 37° C. for one hour; subsequently, a potent inhibitor of cell secretion (like Brefeldin A) is added, and cells are allowed to incubate overnight.

In step (iii), immunofluorescence staining of control or stimulated cultures (Ag-Sp) is performed as previously described (Amicosante et al 2002). In order to identify T lymphocytes cells are stained with monoclonal anti-CD3 antibodies that specifically bind to antigens present on the surface of T cells. To our purpose, we prefer to use anti-D3 antibodies and/or anti-CD4 to identify the CD4+ T lymphocytes, those directly involved in the response to the MTB antigens used in the present invention. In order to assess the response to stimulation, evaluated in terms of IFN-gamma production, antibodies directed against this cytokine are used for intracellular staining.

The following monoclonal antibodies, directed against human antigens, are used to perform the test: fluorescein (FITC)-conjugated anti-IFN-gamma; phycoerythrin (PE)-conjugated anti-CD3 and a FITC-conjugated isotype-matched (IgG1) control antibody. All antibodies are used at a concentration of 0.25 µg/mL. Each new lot of antibodies is tested, and "eppendorf" tubes containing aliquots of the different antibody mixtures (mix) are prepared. In particular, each antibody is tested and used under saturating conditions, to avoid unhomogenous staining of samples. Tubes are then placed in the lyophilizer (Speedvac) and allowed to dry thoroughly (20 min). Each mix is reconstituted with saline immediately before use, and added to the tube containing the cells to be analysed.

In step (iv), samples are acquired and analysed by the use of a flow cytometer with a constant instrument setting, obtained by carefully calibrating the instrument daily, using fluorescent beads and standard procedures that an expert in the field is certainly capable of using. Thus, FACS of the simultaneous presence of T lymphocytes' differentiation markers and of intracellular accumulation of IFN-gamma, allows obtaining results that are both qualitative and quantitative.

Finally, in step (v), test results are expressed both at the qualitative (presence/absence of Ag-Sp T lymphocytes) and quantitative (percentage and frequency per μL of blood) levels. The sensitivity limit of the flow cytometer allows for the detection of differences in percentage of 0.02%. Anyway, it is advisable to perform an accurate analysis in every laboratory to establish a normality range.

TABLE 16

| Reagent | Stimulus and working concentration (values in parentheses relate to concentration in μg/mL) | Concentration of stock solution (mg/mL) | Volume to be added (μL) |
|---|---|---|---|
| 1 | CTR* or DMSO (8) or DMSO (60) | — | — |
| 2 | ESAT-6 protein (5) and CFP-10 protein (5) | 0.05 | 500 |
| 3 | ESAT-6 pooled peptides (50) | 0.1 | 500 |
| 4 | CFP-10 pooled peptides (8) | 0.016 | 500 |
| 5 | ESAT-6 and CFP-10 pooled peptides (58) | 0.12 | 500 |
| 6 | PHA (5) | 0.02 | 500 |
| 7 | PPD (10) | 0.02 | 500 |

*CTR: complete culture medium

Evaluation of Test Results and Diagnostic Response

Figure 5:
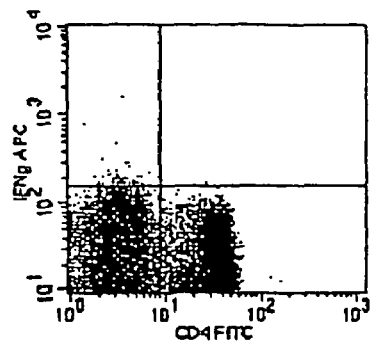
FIG. 5. Response to RD1 selected peptides evaluated by FACS.
Figure 5:
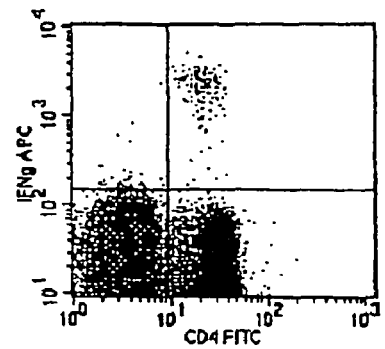

This method, as the previously described one, allows identifying the different types of patients: active tuberculosis patients; patients With a recent tuberculosis infection (contact); latent tuberculosis patients; BCG-vaccinated healthy controls; healthy controls unvaccinated and unexposed to MTB; anergic patients. Monitoring of the efficacy of anti-tuberculosis treatment is also possible using this technique. For example, FIG. 5 shows 2 cytograms referring to one active tuberculosis patient and one healthy control whose PBMC were stimulated with the RD1 selected peptide pools, at T0. The presence of intracellular IFN-gamma is shown on the ordinate, and the CD4+T cells involved in the response to the MTB antigens used in this invention on the abscissa.

The figure shows clearly that in the case of active tuberculosis or recent tuberculosis infection (contact), IFN-gamma-producing CD4+T cells are present (upper right quadrant); on the contrary, these cells are absent from control patients.

Experimental Data Generated using RD1 Selected Peptides and Intact proteins by the ELISPOT Assay in Adult Patients with or without Active Tuberculosis:

To evaluate the assay. 181 subjects were recruited by the National Institute for Infectious Diseases L. Spallanzani:

51 with active tuberculosis (32 males and 19 females, mean age 36±2, 21 Caucasians, 6 Latin Americans, 6 Africans, 11 Eastern Europeans and 7 Asian)

130 without active tuberculosis (69 males and 61 females, mean age 45±2, 112 Caucasians, 3 Latin Americans, 3 Africans, 8 Eastern Europeans and 4 Asian).

The study was approved by an internal ethics committee, and all patients gave written informed consent. All patients with tuberculosis disease had a microbiologically confirmed tuberculosis: 41 pulmonary tuberculosis (culture confirmed) and 10 extra-pulmonary tuberculosis (3 pleuritis, 3 lymph nodes, 1 ovaric, 1 abdominal, 1 kidney, 1 bone) (PCR positive). Among those without active tuberculosis, 50 had a positive TST result and 80 were TST negative.

Figure 6:
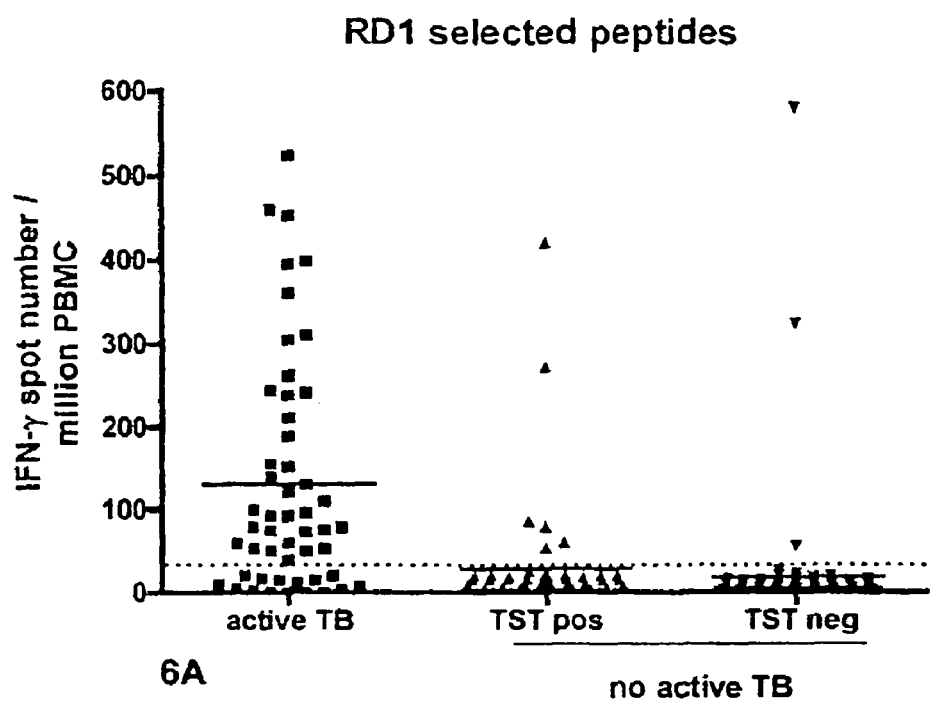
FIG. 6. Response evaluated by ELISPOT to (FIG. 6A) RD1 selected peptides and to (FIG. 6B) RD1 intact proteins. Based on the ROC analysis a cutoff value was calculated: for the peptide stimulation is 34 spot forming cells (SFC) per million PBMC, whereas for the protein stimulation is 36 SFC per million PBMC.
Figure 6:
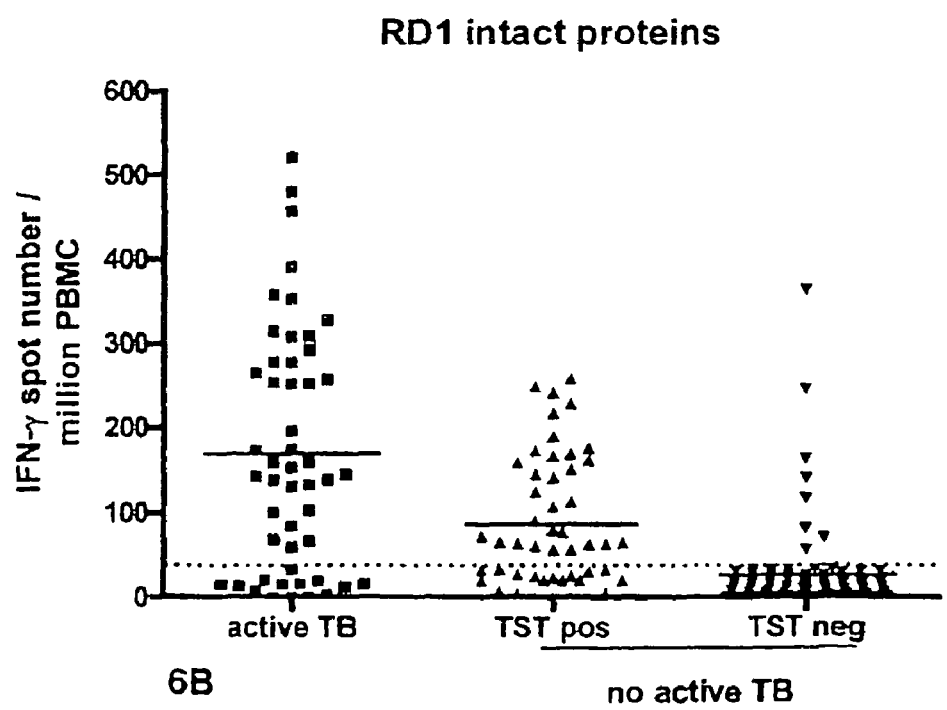

The data in FIG. 6A show that 37/51 of patients with active tuberculosis (73% sensitivity) and 9/130 of those without active tuberculosis (93% specificity) responded in vitro to the selected peptides either alone or in mixture (SEQ 2, 4, 6, 8, 10 and 12), indicating that the response to these selected peptides is associated to active tuberculosis. On the other hand the response to the RD1 intact proteins (FIG. 6B) is found in 36/51 (71%) of patients with active tuberculosis and in 38/130 (29%) of those without active tuberculosis. In particular the RD1 intact proteins response is found in 30/50 (60%) of TST-positive individuals and in 8/80 (10%) of those TST-negative. These results indicate that the response to RD1 intact proteins is associated to tuberculosis infection, more than to active disease.

It is pertinent that among the 80 subjects without active tuberculosis, 32 had a history of previous active tuberculosis successfully treated (previous tuberculosis dated 1-33 years before) and in relation to the TST tests, a previous tuberculosis history was recorded in 23/50 of TST-positive and 9/80 of TST-negative. This indicates even more that the RD1 selected peptides response is specifically associated to active tuberculosis and not to a previous history of disease. The data reported have been generated using RD1 selected peptides pool.

It is important to mention as a technical note that the stimulation with the mixture of RD1 selected peptides, as opposed to using single peptides-separately, provides the best results in terms of sensitivity, reduction of experimental complexity (lower number of samples), and size of the blood sample required for the test. In particular in terms of sensitivity, among those with active tuberculosis responding to the RD1 selected peptides pool, the percentage of responders to single peptides ranges between 10-80%, as shown in FIG. 1A Experimental Comparison to other RD1-based Immunological Diagnostic Tests A comparison was made between the results obtained by our home made ELISPOT assay and those obtained by two RD1-based tests commercially proposed for the diagnosis of tuberculosis infection: T SPOT-TB (Oxford Immunotec, Oxford, UK) and QuantiFERON-TB Gold (Cellestis Limited, Carnagie, Victoria, Australia) (Pai et al 2004, Mori et al 2004). In the commercially available assays, tuberculosis antigens consist in RD1 (ELATE and CFP-10) overlapping peptides spanning the whole proteins. By using techniques such as ELISPOT and whole blood ELISA respectively, both tests evaluate cell mediated immune response to *M. tuberculosis* antigens and have been proposed as assays that may eventually replace the TST because more sensitive, specific and easier to perform (Ravn et al, 2004; Brock et al, 2004).

68 patients were enrolled over 6 months:

27 patients resulted with active tuberculosis and 41 without active tuberculosis PBMC from all patients were run in parallel by our home made RD1 intact proteins and selected peptides ELISPOT assay, T Spot-TB and QuantiFERON-TB Gold (table 17).

In our home made ELISPOT assay, the response to RD1 selected peptides was scored as positive in 20/27 (74%) of those with active tuberculosis and in 3/41 (7%) among those without active tuberculosis (3/21 among TST-positive subjects and 0/20 among TST-negative individuals). Thus, in the population studied, the sensitivity of RD1 selected peptides assay for active tuberculosis was 74% and the specificity 93%. A positive response to RD1 intact proteins was found in 23/27 (85%) of those with active tuberculosis and in 16/41 (39%) among those without active disease (14/21 TST-posftive subjects and 2/20 TST-negative individuals). Thus, sensitivity of RD1 intact proteins assay for active tuberculosis was 85% and the specificity 61%.

A positive response to T SPOT-TB was found in 25/27 (93%) of those with active tuberculosis and among those without active tuberculosis in 16/41 (39%) (14/21 TST-positive subjects and in 2/20 TST-negative individuals). A positive response to QuantiFERON-TB Gold was found in 24/27 (89%) patients with active tuberculosis and among those without active tuberculosis in 13/41 (32%) (11/21 TST-positive subjects and in 2/20 TST-negative individuals).

Taking together both groups of patients with or without active tuberculosis, no significant difference in the proportion of positive responses between the results obtained by our home made RD1 intact proteins ELISPOT assay and the two commercially available tests was found. However, these assays do not discriminate active tuberculosis and latent tuberculosis, a distinction that is required for better global control of the disease. In contrast, our RD1 selected peptides assay is able to provide more specific information regarding tuberculosis disease and infection.

This is proven by the results shown in Table 17A-B.

TABLE 17B-continued

Sensitivity, specificity and diagnostic odds ratio evaluated in individuals with or without active tuberculosis by our home made RD1 selected peptides and intact proteins ELISPOT assay, T SPOT-TB, QuantiFERON-TB Gold assay.

| Assay | Sensitivity (95% CI) | Specificity (95% CI) | Diagnostic Odds ratio (95% CI) |
|---|---|---|---|
| QuantiFERON-TB Gold | 83% (61-95 | 59% (41-76) | 7 (2-25) |

Footnotes:
TB: tuberculosis;
RD1: region of difference;
CI: confidence interval.

Experimental Data Showing Method of Diagnosis of RD1 Selected Peptides and Intact Proteins by the Whole Blood ELISA Assay and FACS Analysis in Patients with or without Active tuberculosis To perform the diagnostic test, in addition to the ELISPOT technique described above, we used the enzyme-linked immunosorbent assay (ELISA) (performed on plasma samples after stimulation of whole blood with the specific antigens), and FACS analysis (performed on mononuclear cells obtained from peripheral blood and cultivated in the presence of the specific antigens).

TABLE 17A

Comparison of the different assays to perform immune diagnosis of tuberculosis

| | Assay | Active TB positive response over total (%) | No Active TB TST-positive Positive response Over total (%) | TST-negative positive response over total (%) | Total (TST-positive and TST-negative) positive response over total (%) |
|---|---|---|---|---|---|
| Home made assay | RD1 Selected peptides | 20/27 (74) | 3/21 (14) | 0/20 (0) | 3/41 (7) |
| | RD1 intact proteins (control) | 23/27 (85) | 14/21 (67) | 2/20 (10) | 16/41 (39) |
| Commercially Available assays | T SPOT-TB | 25/27 (93) | 14/21 (67) | 2/20 (10) | 16/41 (39) |
| | QuantiFERON-TB Gold | 27/27 (89) | 11/21 (52) | 2/20 (10) | 13/41 (32) |

TABLE 17B

Sensitivity, specificity and diagnostic odds ratio evaluated in individuals with or without active tuberculosis by our home made RD1 selected peptides and intact proteins ELISPOT assay, T SPOT-TB, QuantiFERON-TB Gold assay.

| Assay | | Sensitivity (95% CI) | Specificity (95% CI) | Diagnostic Odds ratio (95% CI) |
|---|---|---|---|---|
| Home made assay | RD1 Selected peptides | 70% (47-87) | 91% (75-98) | 22 (5-97) |
| | RD1 Intact proteins | 83% (61-95) | 56% (38-74) | 6 (2-22) |
| Commercially available assays | T SPOT-TB | 91% (72-99) | 59% (41-76) | 15 (3-77) |

Figure 7:
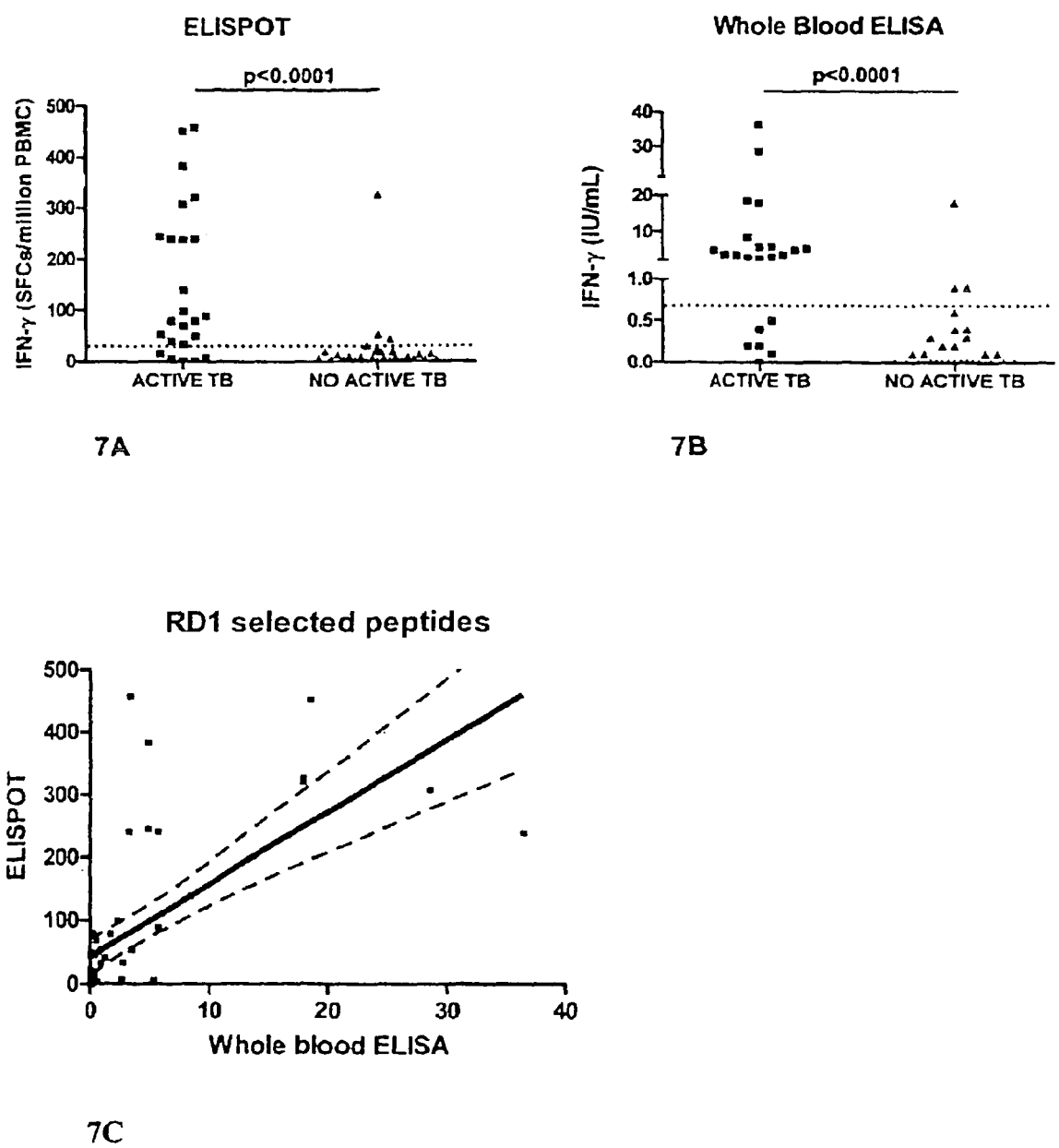
FIG. 7. Comparison between the responses to RD1 selected peptides evaluated by whole blood ELISA assay (FIG. 7A) and by ELISPOT assay (FIG. 7B); linear regression curve between data from the same samples obtained by whole blood ELISA and ELISPOT assays (FIG. 7C).

We then compared the results obtained using the ELISPOT technique with those obtained by ELISA on plasma samples after whole blood stimulation, using RD1 selected peptides. Sensitivity and specificity of the two techniques were quite similar. The data on whole blood assay referring to 24 patients with active tuberculosis microbiologically confirmed (16 with pulmonary tuberculosis and 8 with extra-pulmonary tuberculosis) and 29 without active tuberculosis are shown in FIG. 7A. The sensitivity of the whole blood assay is 71% and the specificity is 90%. The samples have been run simultaneously by ELISPOT (FIG. 7B) with 79% sensitivity and 93% specificity. If we calculate the regression curve (FIG. 7C), there is a significant agreement between the data generated by the 2 methods ($p<0.001$) with $r=0.67$ and with $k=0.67$ (agreement beyond chance).

Moreover, we have confirmed these results by FACS analysis in a small group of patients, and we report here a significant case (FIG. 5). The figure shows that, after stimulation with RD1 selected peptides, the frequency of CD4+IFN-gamma-producing cells in a patient with microbiologically confirmed active tuberculosis is 0.45%. while in a control patient is 0.02%. This difference is highly significant Data Generated Showing the use of RD1 Selected Peptides in Tracing Recent tuberculosis Infection As has been mentioned already, tracing contacts of sputum positive patients is a major public health problem when trying to control tuberculosis in a large population, as well as confusion due to earlier diagnosis and treatment of infected individuals. The diagnosis of tuberculosis infection is traditionally based on TST chest radiography and clinical examination. In addition it is not always possible to perform a chest x-ray (pregnancy, children, etc). Thus it would be important to find rapid, specific and safe assay to trace tuberculosis-infected individuals and their status.

Consequently we evaluated the performance of our assay in studying subjects exposed to a proven sputum-positive tuberculosis case. We enrolled 14 subjects who had been exposed to a microbiologically confirmed tuberculosis case (sputum sample: RNA probe and positive culture results for *M. tuberculosis*). At the time of tuberculosis diagnosis of the sputum-positive patient, the 14 exposed individuals have been evaluated on the basis of:

a) TST;

b) immune diagnostic assay to evaluate:
  1) the response to RD1 intact proteins and selected peptides by ELISPOT,
  2) OF-TB Gold (Cellestis, South Melbourne, Australia); (whole blood ELISA using overlapping peptides);

c) chest radiography and clinical evaluation.

QF-TB Gold involves the use of RD1 overlapping peptides spanning the whole length of RD1 proteins (Ravn et al, 2004; Brock et al, 2004). The QF-TB Gold assay has been recently proposed by the FDA as an whole blood ELISA diagnostic method that may eventually replace the TST because it is more sensitive, specific and easier to perform (Ravn et al, 2004; Brock et al, 2004).

The results are summarised in Table 18. The selected peptides response correlated with a TST larger than 15 mm. These data can have a clinical importance because it has been previously shown a higher risk of developing active TB associated with the degree of TST (Girardi et al, 1997; Fine et al, 1994; Edwards et al, 1973). Thus, in contacts of sputum positive *M. tuberculosis* the response to either RD1 intact proteins or QF-TB Gold may indicate a status of tuberculosis infection whereas the RD1 selected peptides-specific response indicates a higher risk of developing active tuberculosis during whole life time and probably a recent infection.

TABLE 18

Response to RD1 intact protein and selected peptides in healthy contacts of a sputum-positive tuberculosis patient.

|  | Positive/total |
|---|---|
| TST ≧10 mm | 6/14 |
| TST >15 mm | 3/14 |
| Ex vivo response to RD1 selected peptides by ELISPOT | 3/14 |
| Ex vivo response to RD1 intact proteins by ELISPOT | 5/14 |
| QF-TB Gold | 5/14 |
| Clinical evaluation | 0/14 |
| Chest X-ray | 0/14 |

Experimental Data Showing Present Method's Use in Monitoring Efficacy and/or Failure of Anti-Tuberculosis Therapy In order to evaluate the performance of our assay in monitoring the efficacy of anti-TB treatment, on 18 patients with active tuberculosis disease who responded in vitro to RD1 selected peptides at T0 (i.e. the time of diagnosis and commencement of therapy), the ELISPOT has been repeated at T1 (i.e. 3 months later). The patients also underwent clinical, radiological and laboratory evaluation.

Figure 8:
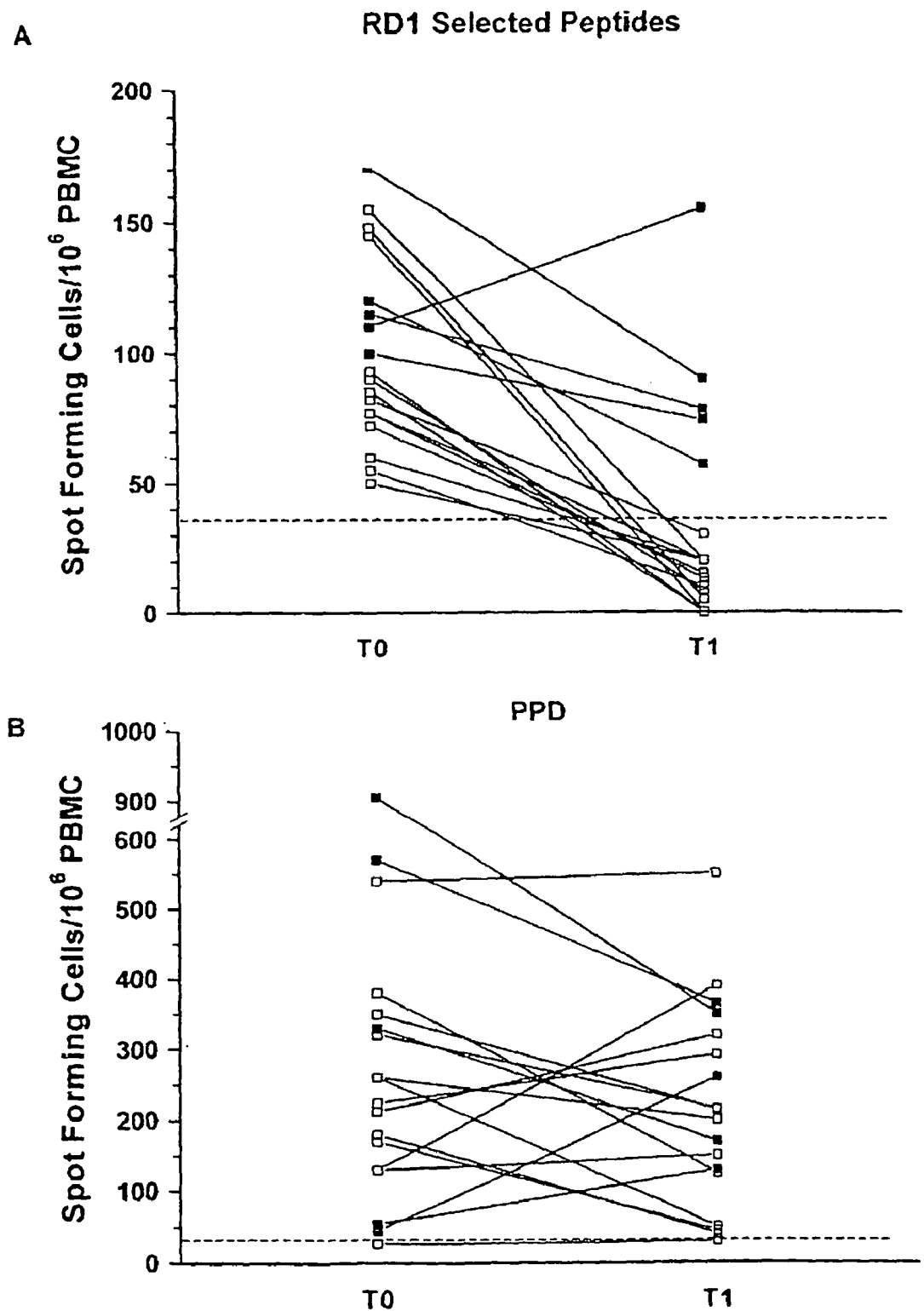
FIG. 8. Response to RD1 selected peptides (FIG. 8A) and to PPD (FIG. 8B) in patients with active tuberculosis, evaluated by ELISPOT. T0: time of tuberculosis diagnosis; T1: after 3 months of anti-tuberculosis therapy. Black squares: symptomatic/culture positive at T1(no responders to anti-tuberculosis therapy). White squares: asymptomatic culture negative at T1(responders to anti-tuberculosis therapy).

As shown in FIG. 8A, the response to the RD1 selected peptides in 13 patients identified as "responders to therapy" (of whom 7 sputum-positive TB cases, whose sputum samples subsequently became negative for *M. tuberculosis*, and 6 extra-pulmonary TB cases), was below the cut-off value (34 SFC per million PBMC). Contrary to this, a positive response to these peptides was still detected in the 5 patients identified as "non responders to therapy" at T1 (p<0.0001 compared to responders). Three of these patients had pulmonary TB and sputum cultures still positive for *M. tuberculosis* (2 were HIV+ and one of them was receiving anti-retroviral therapy), and 2 had extra-pulmonary TB with positive blood and pleural fluid cultures (one of them was HIV+ and not receiving anti-retroviral therapy). From the clinical point of view, these patients were severely affected at T0, in terms of disease extension and malnutrition. On the contrary, immune response to PPD were widely present at T1 in both groups of patients (FIG. 8B), as the response to RD1 intact proteins (data not shown). Thus the response to either PPD (FIG. 4B) or intact ESAT-6 do not correlate with the clinical status of subjects. After 3 further months of therapy, the 5 patients who did not respond to therapy at T1 were reevaluated clinically; they had resolved the disease and the culture tests carried out on their body fluids were negative for *M. tuberculosis*. Moreover, the response to RD1 selected peptides was also negative (data not shown).

In conclusion, in this part of the study we have demonstrated that our immune diagnostic assay based on the response to RD1 selected peptides can be used for diagnosing active tuberculosis and recent MTB infection (contact), and for monitoring the efficacy of anti-tuberculosis treatment. This application is particularly feasible due to the fact that we provide a cut-off, differently from previous reports in which it was reported the possibility to monitor drug efficacy based on a vaguely "decrease" of the response. In fact in the case of active tuberculosis, the response to the peptides persists in tuberculosis subjects who do not respond to the specific anti-tuberculosis treatment, while it becomes negative after 3 months of effective therapy. One possible explanation is that only in the presence of viable and actively replicating bacilli, MTB-secreted proteins, like RD1 proteins, can induce IFN-gamma production by T cells, and this situation is present in subjects with active tuberculosis and in subjects with recent infection. On the contrary, in the case of healthy contacts 3 months after exposure to MTB, or in the case of active tuberculosis after effective therapy, the bacterium stops replicating and the immune response to selected epitopes becomes undetectable, at least with our assay. Nevertheless, there is a persisting, and probably lifelong, in vitro response to RD1 intact proteins, indicative of latent tuberculosis infection.

Application of the Invention to Target Patient Groups:

The present invention's application is a reliable and swift diagnosis of tuberculosis. Therefore, It was tested on 3 target patient groups that would conceivably benefit from this invention. It is not in any way limited to these groups. It was tested on:

a) Children
b) Health care workers
c) Immuno-compromised patients (HIV+ patients)

a) Data Generated using RD1 Selected Peptides and Intact Proteins in Children with or without Active Tuberculosis With the increased incidence of tuberculosis in the world population, the number of tuberculosis cases in a childhood population has been estimated to increase exponentially and to reach 40% of total cases. In the developed countries with a lower incidence of tuberculosis, childhood tuberculosis represents less than 5% of all cases (Shingadia et al 2003). A diagnosis of childhood tuberculosis is a warning event within a community that suggests a recent transmission, most commonly from an infectious adult with pulmonary or cavitary tuberculosis. The accurate determination of the public health dimensions of childhood tuberculosis are thus important both with respect to overall tuberculosis control in the population, and for earlier diagnosis and treatment of children through identification of infectious adult cases. The diagnosis of tuberculosis in children is traditionally based on chest radiography. TST, tuberculosis staining/culture although all these investigations may not always be positive in children with tuberculosis. Thus immune diagnostic assays may be useful in helping the clinicians in the diagnosis (Shingadia et al 2003). To evaluate the performance of our assay in children we have studied 12 children with a suspect of active tuberculosis [age range: 1-15 years (mean 4.5 y)]; 9 coming from areas at high risk of tuberculosis. In 6 of them a pulmonary tuberculosis was diagnosed (in 4 was microbiologically diagnosed and in 2 was clinically diagnosed). In table 19, the results obtained by ELISPOT assay (and reproduced by whole blood assay, data not shown) are reported. The data suggest that the response to RD1 selected peptides is associated to active tuberculosis whereas the response to RD1 intact proteins is to a general tuberculosis infection, as previously demonstrated in adults (table 17 A-B). All children with active tuberculosis had a positive response to TST, but, as previously mentioned, TST (that is presently used to support the diagnosis of active tuberculosis in patients without microbiological confirmation of the disease) has a limited specificity and does not discriminate between latent infection and active tuberculosis (Fine et al 1999, Huebner et al 1993, American Thoracic Society 2000). It is also worth noting that BCG vaccination does not alter the assay specificity, as shown by the fact that 3/6 were BCG-vaccinated and none of them responded to the RD1 selected peptides.

TABLE 19

Results obtained in children with or without active diseases in terms of response to RD1 proteins and selected peptides by ELISPOT assay. TST responses and the number of BCG-vaccinated individuals are reported.

|  | RD1 intact proteins | RD1 selected peptides | TST | BCG |
| --- | --- | --- | --- | --- |
| Active TB |  |  |  |  |
| Positive over total | 5/6 | 4/6 | 6/6 | 3/6 |
| % | 83 | 67 | 100 | 50 |
| No Active TB |  |  |  |  |
| Positive over total | 2/6 | 0/6 | 2/6 | 3/6 |
| % | 33 | 0 | 33 | 50 | b) Data Generated using RD1 Selected Peptides and Intact Proteins in Tracing Health Care Workers (HCW)

Health care workers (HCW) are a particular important group to study when evaluating latent tuberculosis infection, because their risk of acquiring latent tuberculosis is higher than average as a result of their exposure to patients with tuberculosis. In addition, should HCW develop active tuberculosis, they are at high risk of transmitting the infection to their patients, including those patients who are immuno-compromised (Gershon et al 2004). Consequently, it is important to evaluate accurately the status of tuberculosis infection in this group.

Our aim was to evaluate the status of tuberculosis infection by 2 different tests, by ELISPOT assay using both RD1 intact protein and selected peptides and by a whole blood commercial kit (QF-TB Gold) (Ravn et al, 2004; Brock et al, 2004). The QF-TB Gold involves the use of RD1 overlapping peptides spanning the whole length of RD1 proteins (Ravn et al, 2004; Brock et al, 2004). The QF-TB Gold assay was included in the study because it has been proposed as an whole blood ELISA that may eventually replace the TST because more sensitive, specific and easier to perform (Ravn et al, 2004; Brock et al, 2004).

We have enrolled 100 health care workers (HCW) from 3 different hospitals located in Roma, Italy. HCW of group 1 (19 subjects) and 2 (38 subjects) are dealing with patients with active tuberculosis (pneumology wards and infectious disease wards, respectively) whereas HCW of group 3 (43 subjects) came from another hospital ward, with a low risk for tuberculosis (group B).

The results indicate that the response to RD1 intact proteins evaluated by ELISPOT assay is similar to the response evaluated by the QF-TB Gold, whereas the response to RD1 selected peptides is found only in a small percentage of the HCW. In particular 28% (28/100) responded to the intact proteins and 23% (23/100) to the QF-TB Gold assay. In contrast the response to the selected peptides was 11% (11/100) (table 7A).

To substantiate these data, among those QF-TB Gold positive, (assay that is going to be considered the gold standard for tuberculosis infection), we identified 10 HCW that were peptide positive and 13 HCW peptide negative. Among those peptide positive 7/10 had a TST>10 mm (70%), whereas only 5/13 HCW peptide negative had a TST>10 (38%). In contrast, among those QF-TB Gold negative only 8/77 (10%) showed a larger TST (table 20B). These data can have a clinical importance because it has been previously shown a higher risk of active tuberculosis associated with the degree of TST (Girardi et at, 1997; Fine et al, 1994: Edwards et al, 1973). Thus, in HCW the response to either intact proteins or QF-TB Gold may indicate a status of tuberculosis infection whereas the peptides-specific response a higher risk of developing active TB during whole life time.

TABLE 20A

MTB-specific responses evaluated by RD1 intact proteins and selected peptides by ELISPOT assay and QF-TB Gold in 3 groups of HCW.

| HCW GROUP | SUBJECTS | RD1 ELISPOT assay INTACT PROTEINS positive over total (%) | RD1 ELISPOT assay SELECTED PEPTIDES positive over total (%) | Whole Blood ELISA QF-TB GOLD Positive over total (%) |
|---|---|---|---|---|
| 1 | 19 | 7 (37) | 1 (5) | 5 (26) |
| 2 | 38 | 15 (39) | 7 (18) | 10 (26) |
| 3 | 43 | 6 (14) | 3 (7) | 8 (19) |
| TOTAL | 100 | 28 (28) | 11 (11) | 23 (23) |

TABLE 20 B

Correlation between MTB-specific responses and TST in HCW.

| HCW groups (total subjects) | TST ≧10 mm Positive over total (%) |
|---|---|
| QF-TB Gold positive and selected peptides positive (10) | 7/10 (70%) |
| QF-TB Gold positive and selected peptides negative (13) | 5/13 (38%) |
| QF-TB Gold negative (77) | 8/77 (10%) | c) Data Generated using RD1 Selected Peptides and Intact Proteins in HIV Positive Patients with or without Active Tuberculosis Tuberculosis incidence has increased worldwide and the most profound influence on tuberculosis incidence is HIV infection, particularly in sub-Saharan Africa where HIV and tuberculosis form a lethal combination. Each infection accelerates the other's progress. HIV infection has been estimated to account for an excess of 34% of new cases (Schulzer et al, 1992). Thus to evaluate our assays' efficiency, we recruited at our institute 65 subjects with HIV Infection. In 15 (23%) of them, no response to the mitogen (PHA) was found and thus they were excluded from the analysis (anergic patients). In vitro IFN-gamma response to RD1 intact proteins and their selected peptides and milogens was evaluated in PBMC by ELISPOT assay. Of the patients enrolled, 32 (52%) were diagnosed with microbiologically confirmed tuberculosis. In vitro anergy was present in 28% of patients with active tuberculosis and in 21% of those without tuberculosis. Cell anergy was correlated with a reduced CD4 cell number and high HIV load.

Among non-anergic patients, 18126 with tuberculosis and 0/24 without tuberculosis had a positive response to selected peptides. Thus, sensitivity of our assay is 74%, specificity is 100%. TST was positive only in 6/26 tuberculosis patients and in 6/24 without tuberculosis (table 21). The difference of response to the selected peptides and TST was statistically significant ($p<0.001$). In conclusion, in HIV+ individuals without in vitro anergy, this immune diagnostic assay based on RD1 selected peptides, although with a still sub-optimal sensitivity provides rapid and specific diagnostic information. In addition our assay based on RD1 selected peptides is significantly more sensitive than TST.

TABLE 21

Correlation between RD1 selected peptides responses and TST.

| | HIV+ Active tuberculosis patients | |
|---|---|---|
| | Selected peptides | TST |
| Positive | 18 | 6 |
| Negative | 8 | 20 |

REFERENCES

American Thoracic Society. Diagnostic standards and classification of tuberculosis in adults and children. Am J Respir Crit Care Med 2000, 161:1376-1395.

American Thoracic Society. Rapid diagnostic tests for tuberculosis: what is the appropriate use? Am. J. Respir. Crit. Care Med. 1997:155:1804-1811

Amicosante M, Gioia C. Montesano C, Casetti R. Topino S, D'Offizi G, Cappelli G, Ippolito G, Colizzi V, Poccia F, Pucillo L P. Computer-based design of an HLA-haplotype and HIV-clade independent cytotoxic T-lymphocyte assay for monitoring HIV-specific immunity. Mol Med 2002, 8:798-807.

Andersen P, Andersen A B, Sorensen A L, Nagai S. Recall of long-lived immunity to *Mycobacterium tuberculosis* infection in mice. J Immunol 1995; 154:3359-3372.

Andersen P, Heron I. Specificity of protective memory immune response against *Mycobaterium tuberculosis*. Infect Immun 1993; 61:844-851.

Andersen P. TB vaccines: progress and problems. TRENDS in Immunology 2001; 22:160-168.

Brock I et al. Comparison of tuberculin skin test and new specific blood test in tuberculosis contacts. AJRCCM 2004; 170:65-69.

Case definitions for infectious conditions under public health surveillance. CDC MMWR Recommendation and Reports 1997, 46:40-41.

Cockle P J, et al. Identification of novel *M. tuberculosis* antigents with potential as diagnostic reagents or subunit vaccine candidates by comparative genomics. Infection and Immunity 2002; 6696-7003.

Doherty T M, Demissie A, Olobo J, Wolday D, Britton S, Eguale T, Ravn P, Andersen P. Immune responses to the *Mycobacterium tuberculosis*-specific antigen ESAT-6 signal subclinical infection among contacts of tuberculosis patients. J Clin Microbiol 2002; 40:704-706.

Dye C, Scheele S. Dolin P, Pathania V, Raviglione M C. Consensus statement. Global burden of tuberculosis: estimated incidence, prevalence, and mortality by country. WHO Global surveillance and Monitoring Project. JAMA 1999; 282:677-686.

Edwards L B, Acquaviva F A, Livesay V T. Identification of the tuberculosis infected: dual tests and density of reaction. Am Rev Respir Dis 1973, 108:1334-1339.

Fine P E, Bruce J, Ponnighaus J M, Nkhosa P, Harawa A, Vynnycky E. Tuberculin sensitivity: conversions and reversions in a rural African population. Int J Tuberc Lung Dis 1999, 3:962-975.

Fine P E M, Sterne J A C, Ponnighaus J M, Rees R J. Delayed type hypersensitivity, mycobacterial vaccines and protective immunity. Lancet 1994, 344:1245-1249.

Fleckenstein B, Jung G, Wiesmüller K H. Quantitative analysis of peptide-MHC class II interaction. Semin Immunol 1999; 11:405-416.

Gershon A S, McGeer A, Bayoumi A M, Raboud J. Yang J. Health care workers and the initiation of treatment for latent tuberculosis infection. Clin Infect Dis 2004, 39:667-672.

Girardi E, Antonucci G. Ippolito G, Raviglione M C, Rapiti E, Di Perri G, Babudieri S and the Gruppo Italiano di Studio Tubercolosi e AIDS. Association of tuberculosis risk with the degree of tuberculin reaction in HIV-infected patients. Arch Intern Med 1997, 157:797-800.

Harboe M, Oettinger T, Wiker H G. Rosenkrands I, Andersen P. Evidence for occurrence of the ESAT-6 protein in *Mycobacterium tuberculosis* and virulent *Mycobacterium bovis* and for its absence in *Mycobacterium bovis* BCG. Infect Immun 1996; 64:16-22.

Huebner R E, Schein M F, Bass J B Jr. The tuberculin skin test. Clin Infect Dis 1993, 17:968-975.

Lalvani A, Pathan A A, Durkan H, Wilkinson K A, Whelan A, Deeks J J, Reece W H, Latif M, Pasvol G, Hill A V. Enhanced contact tracing and spatial tracking of *Mycobacterium tuberculosis* infection by enumeration of antigen-specific T cells, Lancet 2001; 357:2017-2021. a)

Lalvani A, Nagvenkar P, Udwadia Z, Pathan A A, Wilkinson K A, Shastri J S, Ewer K, Hill A V, Mehta A, Rodrigues C. Enumeration of T cells specific for RD1-encoded antigens suggests a high prevalence of latent *Mycobacterium tuberculosis* infection in healthy urban Indians. J Infect Dis 2001; 183:469477. b)

Lalvani A, Pathan M, McShane H, Durkan H., Wilkinson K A., Whelan A., Deeks J. J., Reece W. H. H., Latif M., Pasvol G., Hill A. V. S. Rapid detection of *Mycobacterium tuberculosis* infection by enumeration of antigen-specific T cells. Am J Respir Crit Care Med 2001; 163:824-828. c)

Mahairas G G, Sabo P J, Hickey M J, Singh D C, Stover C K. Molecular analysis of genetic differences between *Mycobacterium bovis* BCG and virulent *M. bovis*. J Bacteriol 1996; 178:1274-1282.

Mori T. Sakatani M, Yamagishi F, et al. Specific Detection of Tuberculosis Infection with an Interferon-gamma Based Assay using New Antigens. AJRCCM 2004; 170:59-64.

Pai M, Riley L W, Colford J M Jr. Interferon-gamma assays in the immunodiagnosis of tuberculosis: a systematic review. Lancet Infect Dis 2004:4:761-76.

Pathan A A, Wilkinson K A, Klenerman P, McShane H., Davidson R. N., Pasvol G., Hill A. V. S. Lalvani A Direct ex vivo analysis of antigen-specific IFN-gamma-secreting CD4 T cells in *Mycobacterium tuberculosis*-infected individuals: association with clinical disease state and effect of treatment. J Immunol 2001: 167:5217-5225. b)

Pollock J M, Andersen P. Predominant recognition of the ESAT-6 protein in the first phase of interferon with *Mycobacterium bovis* in cattle. Infect Immun 1997; 65:2587-2592. Proceedings of the 12th IHWC. HLA Genetic diversity of HLA Functional and Medical Implication. Edited by Charron D. EDK, Medical and Scientific International Publisher, Paris 1997.

Rammensee H, Bachmann J, Emmerich N P, Bachor O A, Stevanovic S. SYFPEITHI: database for MHC ligands and peptide motifs. Immunogenetics 1999; 50:213-219.

Ravn P. Demissie A, Eguale T, Wondwosson H, Lein D, Amoudy H A, Mustafa A S, Jensen A K, Holm A, Rosenkrands I, Oftung F, Olobo J, von Reyn F, Andersen P. Human T cell responses to the ESAT-6 antigen from *Mycobacterium tuberculosis*. J Infect Dis 1999; 179:637-645.

Ravn P, Munk M E, Andersen A B, Lundgren B, Nielsen L N, Lillebaek T. Soerensen I J, Andersen P, Weldingh K. Reactivation of tuberculosis during immunosuppressive treatment in a patient with a positive QuantiFERON-RD1 test. Scand J Infect Dis. 2004; 36(6-7):499-501.

Richeldi L. et al. Early diagnosis of subclinical multi-drug-resistant tuberculosis. Ann intern Med. 2004; 140:709-713.

Richeldi L. et al. T cell-based tracking of multidrug resistant tuberculosis infection following brief exposure. AJRCCM 2004; 170:288-95.

Schulzer M, Fitzgerald J, Enarson D, Grzybowski S. An estimate of the future size of the tuberculosis problem in sub-Saharan Africa resulting from HIV infection. Tuber Lung Disease 1992, 73:52-58.

Shingadia D and Novelli V. Diagnosis and treatment of tuberculosis in children. Lancet Infect Dis 2003, 3:624-632.

Singh H, Raghava G P. ProPred: prediction of HLA-DR binding sites. Bioinformatics 2001; 17:1236-1237.

Sturniolo T, Bono E, Ding J, Raddrizzani L, Tuereci O, Sahin U. Braxenthaler M, Gallazzi F, Protti M P, Sinigaglia F, Hammer J. Generation of tissue-specific and promiscuous HLA ligand database using DNA microarrays and virtual HLA class II matrices. Nat Biotechnol 1999; 17:555-561.

Ulrichs T, Munk M E, Mollenkopf H, Behr-Perst S, Colangeli R, Gennaro M L, Kaufmann S H. Differential T cell responses to *Mycobacterium tuberculosis* ESAT6 in tuberculosis patients and healthy donors. Eur J Immunol 1998; 28:3949-3958.

Van Pinxteren L A et al. Diagnosis of tuberculosis based on the 2 specific antigens ESAT-6 and CFP-10. Clin Diagn Lab Immunol 2000; 155-160.

Vincenti D, Carrara S, De Mori P, Pucillo L P, Petrosillo N, Palmieri F, Armignacco O. Ippolito G, Girardi E, Amicosante M, Goletti D. Identification of ESAT-6 Epitopes for the Immunodiagnosis of Active Tuberculosis. Mol Med 2003; 9: 105-111.

PATENTS REFERENCED

EP 1 350 839 A;
US2004058399;
WO 01/04151 A;
WO 01/79274 A;
WO 03/093307 A
WO 2004/099771,
WO 97/09428 A;
WO 99/04005;
WO 99/42076 A:
WO 00/26248;
WO 02059605;
WO 09221697.

---

LIST OF SEQUENCES

SEQ ID NO: 1 corresponding to CFP-10 peptide 18-31
TTCGAGCGGATCTCCGGCGACCTGAAAACCCAGATCGACCAG
SEQ ID NO: 2 FERISGDLKTQIDQ (nucleotidic sequence of CFP-10 peptide 18-31)
SEQ ID NO: 3 corresponding to CFP-10 peptide 41-68
GGCCAGTGGCGCGGCGCGGCGGGGACGGCCGCCCAGGCCGCGGTGGTGCGC
TTCCAAGAAGCAGCCAATAAGCAGAAGCAGGAA
SEQ ID NO: 4 GQWRGAAGTAAQAAVVRFQEAANKQKQE (nucleotidic sequence of CFP-10 peptide 41-68)

LIST OF SEQUENCES

SEQ ID NO: 5 corresponding to CFP-10 peptide 53-68
GCCGCGGTGGTGCGCTTCCAAGAAGCAGCCAATAAGCAGAAGCAGGAA
SEQ ID NO: 6 AAVVRFQEAANKQKQE (nucleotidic sequence of CFP-10 peptide 53-68)
SEQ ID NO: 7 corresponding to CFP-10 peptide 74-86
ACGAATATTCGTCAGGCCGGCGTCCAATACTCGAGGGCC
SEQ ID NO: 8 TNIRQAGVQYSRA (nucleotidic sequence of CFP-10 peptide 74-86)
SEQ ID NO: 9 corresponding to ESAT-6 peptide 6-28
TGGAATTTCGCGGGTATCGAGGCCGCGGCAAGCGCAATCCAGGGAAATGTC
ACGTCCATTCATTCCCTC
SEQ ID NO: 10 WNFAGIEAAASAIQGNVTSIHSL (nucleotidic sequence of ESAT-6 peptide 6-28)
SEQ ID NO: 11 corresponding to ESAT-6 peptide 67-79
AACGCGCTGCAGAACCTGGCGCGGACGATCAGCGAAGCC
SEQ ID NO: 12 NALQNLARTISEA (nucleotidic sequence of ESAT-6 peptide 67-79)

---

The invention claimed is:

1. A peptide composition suitable to discriminate between a) latent tuberculosis infection or tuberculosis under efficacious *M. tuberculosis* therapy and b) active tuberculosis or recent tuberculosis infection or re-infection wherein said peptide composition comprises a pool of CFP-10 peptides which consists of SEQ ID NO: 2, SEQ ID NO: 4, SEQ ID NO: 6, and SEQ ID NO: 8.

2. The composition according to claim 1 further comprising two ESAT-6 peptides consisting of SEQ ID NO: 10 and SEQ ID NO: 12.

3. A diagnostic kit suitable to discriminate between: a) latent tuberculosis infection or tuberculosis under efficacious *M. tuberculosis* therapy, and b) active tuberculosis or recent tuberculosis infection or re-infection, for diagnosing and monitoring states of tuberculosis infection, comprising a peptide composition comprising a pool of CFP-10 peptides consisting of: SEQ ID NO: 2, SEQ ID NO: 4, SEQ ID NO: 6, and SEQ ID NO: 8.

4. A diagnostic kit according to claim 3 wherein said peptide composition comprising a pool of CFP-10 peptides consisting of: SEQ ID NO: 2, SEQ ID NO: 4, SEQ ID NO: 6, and SEQ ID NO: 8, further comprises two ESAT-6 peptides consisting of SEQ ID NO: 10 and SEQ ID NO: 12.

* * * * *

SEQUENCE LISTING

```
<160> NUMBER OF SEQ ID NOS: 12

<210> SEQ ID NO 1
<211> LENGTH: 42
<212> TYPE: DNA
<213> ORGANISM: Mycobacterium tuberculosis
<220> FEATURE:
<221> NAME/KEY: CDS
<222> LOCATION: (1)..(42)
<223> OTHER INFORMATION: CFP-10 18-31

<400> SEQUENCE: 1 ttc gag cgg atc tcc ggc gac ctg aaa acc cag atc gac cag         42
Phe Glu Arg Ile Ser Gly Asp Leu Lys Thr Gln Ile Asp Gln
1               5                   10

<210> SEQ ID NO 2
<211> LENGTH: 14
<212> TYPE: PRT
<213> ORGANISM: Mycobacterium tuberculosis

<400> SEQUENCE: 2

Phe Glu Arg Ile Ser Gly Asp Leu Lys Thr Gln Ile Asp Gln
1               5                   10

<210> SEQ ID NO 3
<211> LENGTH: 84
<212> TYPE: DNA
<213> ORGANISM: Mycobacterium tuberculosis
<220> FEATURE:
<221> NAME/KEY: CDS
<222> LOCATION: (1)..(84)
<223> OTHER INFORMATION: CFP-10 41-68

<400> SEQUENCE: 3 ggc cag tgg cgc ggc gcg gcg ggg acg gcc gcc cag gcc gcg gtg gtg     48
Gly Gln Trp Arg Gly Ala Ala Gly Thr Ala Ala Gln Ala Ala Val Val
1               5                   10                  15 cgc ttc caa gaa gca gcc aat aag cag aag cag gaa                     84
Arg Phe Gln Glu Ala Ala Asn Lys Gln Lys Gln Glu
            20                  25

<210> SEQ ID NO 4
<211> LENGTH: 28
<212> TYPE: PRT
<213> ORGANISM: Mycobacterium tuberculosis

<400> SEQUENCE: 4

Gly Gln Trp Arg Gly Ala Ala Gly Thr Ala Ala Gln Ala Ala Val Val
1               5                   10                  15
```

-continued

Arg Phe Gln Glu Ala Ala Asn Lys Gln Lys Gln Glu
         20                  25

<210> SEQ ID NO 5
<211> LENGTH: 48
<212> TYPE: DNA
<213> ORGANISM: Mycobacterium tuberculosis
<220> FEATURE:
<221> NAME/KEY: CDS
<222> LOCATION: (1)..(48)
<223> OTHER INFORMATION: CFP-10 53-68

<400> SEQUENCE: 5 gcc gcg gtg gtg cgc ttc caa gaa gca gcc aat aag cag aag cag gaa     48
Ala Ala Val Val Arg Phe Gln Glu Ala Ala Asn Lys Gln Lys Gln Glu
1               5                  10                  15

<210> SEQ ID NO 6
<211> LENGTH: 16
<212> TYPE: PRT
<213> ORGANISM: Mycobacterium tuberculosis

<400> SEQUENCE: 6

Ala Ala Val Val Arg Phe Gln Glu Ala Ala Asn Lys Gln Lys Gln Glu
1               5                  10                  15

<210> SEQ ID NO 7
<211> LENGTH: 39
<212> TYPE: DNA
<213> ORGANISM: Mycobacterium tuberculosis
<220> FEATURE:
<221> NAME/KEY: CDS
<222> LOCATION: (1)..(39)
<223> OTHER INFORMATION: CFP-10 74-86

<400> SEQUENCE: 7 acg aat att cgt cag gcc ggc gtc caa tac tcg agg gcc                  39
Thr Asn Ile Arg Gln Ala Gly Val Gln Tyr Ser Arg Ala
1               5                  10

<210> SEQ ID NO 8
<211> LENGTH: 13
<212> TYPE: PRT
<213> ORGANISM: Mycobacterium tuberculosis

<400> SEQUENCE: 8

Thr Asn Ile Arg Gln Ala Gly Val Gln Tyr Ser Arg Ala
1               5                  10

<210> SEQ ID NO 9
<211> LENGTH: 69
<212> TYPE: DNA
<213> ORGANISM: Mycobacterium tuberculosis
<220> FEATURE:
<221> NAME/KEY: CDS
<222> LOCATION: (1)..(69)
<223> OTHER INFORMATION: ESAT-6  6-28

<400> SEQUENCE: 9 tgg aat ttc gcg ggt atc gag gcc gcg gca agc gca atc cag gga aat     48
Trp Asn Phe Ala Gly Ile Glu Ala Ala Ala Ser Ala Ile Gln Gly Asn
1               5                  10                  15 gtc acg tcc att cat tcc ctc                                          69
Val Thr Ser Ile His Ser Leu
            20

<210> SEQ ID NO 10

-continued

```
<211> LENGTH: 23
<212> TYPE: PRT
<213> ORGANISM: Mycobacterium tuberculosis

<400> SEQUENCE: 10

Trp Asn Phe Ala Gly Ile Glu Ala Ala Ala Ser Ala Ile Gln Gly Asn
1               5                   10                  15

Val Thr Ser Ile His Ser Leu
            20

<210> SEQ ID NO 11
<211> LENGTH: 39
<212> TYPE: DNA
<213> ORGANISM: Mycobacterium tuberculosis
<220> FEATURE:
<221> NAME/KEY: CDS
<222> LOCATION: (1)..(39)
<223> OTHER INFORMATION: ESAT-6 67-79

<400> SEQUENCE: 11 aac gcg ctg cag aac ctg gcg cgg acg atc agc gaa gcc              39
Asn Ala Leu Gln Asn Leu Ala Arg Thr Ile Ser Glu Ala
1               5                   10

<210> SEQ ID NO 12
<211> LENGTH: 13
<212> TYPE: PRT
<213> ORGANISM: Mycobacterium tuberculosis

<400> SEQUENCE: 12

Asn Ala Leu Gln Asn Leu Ala Arg Thr Ile Ser Glu Ala
1               5                   10
```